(12) United States Patent
MacQuarrie et al.

(10) Patent No.: US 8,251,911 B2
(45) Date of Patent: *\*Aug. 28, 2012*

(54) MONITORING PHYSIOLOGICAL CONDITION AND DETECTING ABNORMALITIES

(75) Inventors: David MacQuarrie, Langley (CA); Bozena Kaminska, Burnaby (CA)

(73) Assignee: Heart Force Medical Inc., Vancouver, British Columbia (CA)

( * ) Notice: Subject to any disclaimer, the term of this patent is extended or adjusted under 35 U.S.C. 154(b) by 11 days.

This patent is subject to a terminal disclaimer.

(21) Appl. No.: 12/956,643

(22) Filed: Nov. 30, 2010

(65) Prior Publication Data

US 2011/0130670 A1    Jun. 2, 2011

Related U.S. Application Data

(63) Continuation of application No. 11/743,591, filed on May 2, 2007, now Pat. No. 7,846,104.

(60) Provisional application No. 60/888,930, filed on Feb. 8, 2007.

(51) Int. Cl.
*A61B 5/02* (2006.01)

(52) U.S. Cl. ......... 600/481; 600/500; 600/501; 600/508

(58) Field of Classification Search ................. 600/481, 600/500, 501, 508, 513
See application file for complete search history.

(56) References Cited

U.S. PATENT DOCUMENTS

| | | | |
|---|---|---|---|
| 4,838,275 A | | 6/1989 | Lee |
| 5,159,932 A * | | 11/1992 | Zanetti et al. ............... 600/508 |
| 5,964,720 A * | | 10/1999 | Pelz ............................ 600/595 |
| 6,161,038 A * | | 12/2000 | Schookin et al. ............. 600/519 |
| 6,517,492 B2 | | 2/2003 | Koblanski |
| 6,881,191 B2 | | 4/2005 | Oakley et al. |
| 6,937,899 B2 | | 8/2005 | Sheldon et al. |
| 6,963,777 B2 * | | 11/2005 | Lincoln et al. ................. 607/18 |
| 7,035,684 B2 | | 4/2006 | Lee |
| 7,174,203 B2 | | 2/2007 | Arand et al. |
| 7,254,433 B2 | | 8/2007 | Diab et al. |
| 7,485,095 B2 | | 2/2009 | Shusterman |
| 2003/0074144 A1 | | 4/2003 | Freed et al. |
| 2003/0233034 A1 | | 12/2003 | Varri et al. |
| 2004/0029259 A1 | | 2/2004 | McDevitt et al. |
| 2005/0095591 A1 | | 5/2005 | Christoperson et al. |
| 2006/0058673 A1 | | 3/2006 | Aase et al. |
| 2006/0095085 A1 * | | 5/2006 | Marcus et al. ................. 607/17 |
| 2006/0190045 A1 | | 8/2006 | Marcus et al. |
| 2006/0293605 A1 | | 12/2006 | Zanettie et al. |
| 2006/0293714 A1 * | | 12/2006 | Salo et al. ..................... 607/9 |
| 2007/0027489 A1 * | | 2/2007 | Gill et al. ...................... 607/9 |
| 2007/0032749 A1 * | | 2/2007 | Overall et al. ................ 600/595 |

FOREIGN PATENT DOCUMENTS

WO  WO 2004/034896   4/2004

\* cited by examiner

*Primary Examiner* — Carl H Layno
*Assistant Examiner* — Yun Haeng Lee
(74) *Attorney, Agent, or Firm* — Saliwanchik, Lloyd & Eisenschenk

(57) ABSTRACT

A system and method for monitoring an individual's physiological condition and detecting abnormalities therein, comprising concurrently receiving an electrocardiograph signal and a ballistocardiograph signal. The electrocardiograph and ballistocardiograph signals are conditioned to minimize background extraneous noise after which, each signal is concurrently processed and analyzed to detect repeating cyclical patterns and further characterized to identify individual components of the repeating cycles. At least one individual component in one signal is selected as a reference marker or a selected component in the other signal. The two signals are then synchronized, outputs produced therefrom and stored in a database.

30 Claims, 18 Drawing Sheets

Fig. 3
(a) 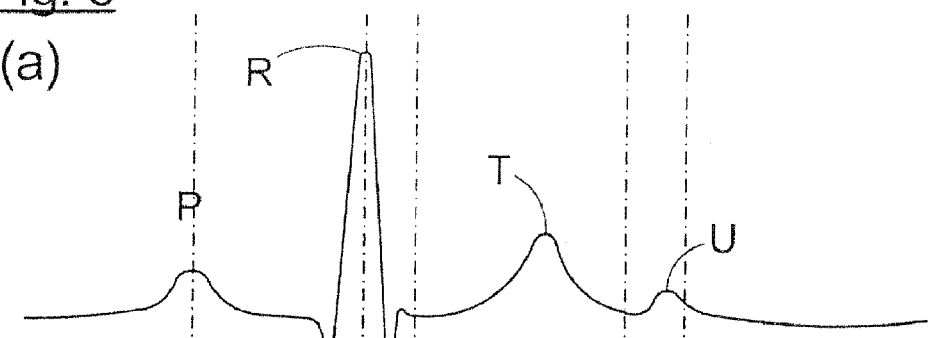
(b) 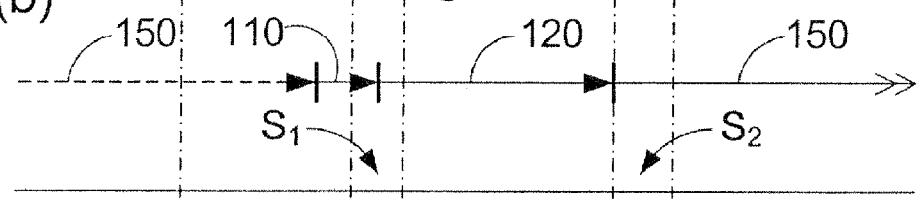
(c) 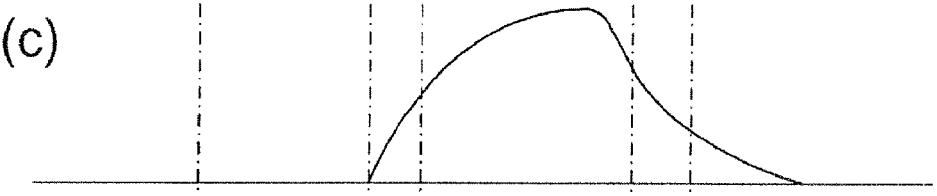
(d) 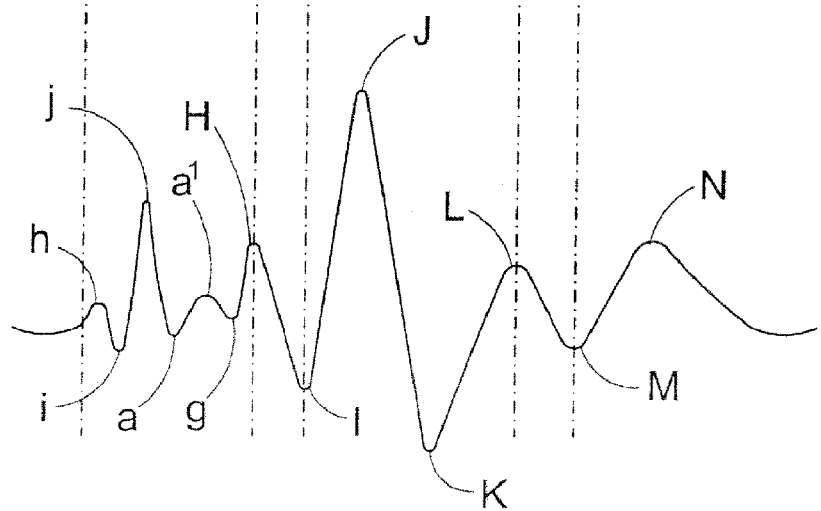

Synchronized cycles of pre-exercise
ECG (top) & BCG (bottom)

Synchronized cycles of post-exercise
ECG (top) & BCG (bottom)

Pre-exercise / post-exercise correlation = 0.9227

1$^{st}$ sec    2$^{nd}$ sec    3$^{rd}$ sec    4$^{th}$ sec

Synchronized cycles of pre-exercise
ECG (top) & BCG (bottom)

Synchronized cycles of post-exercise
ECG (top) & BCG (bottom)

BCG before (dotted) & after (solid) exercise

Pre-exercise / post-exercise correlation = 0.39348

1ˢᵗ sec    2ⁿᵈ sec    3ʳᵈ sec    4ᵗʰ sec

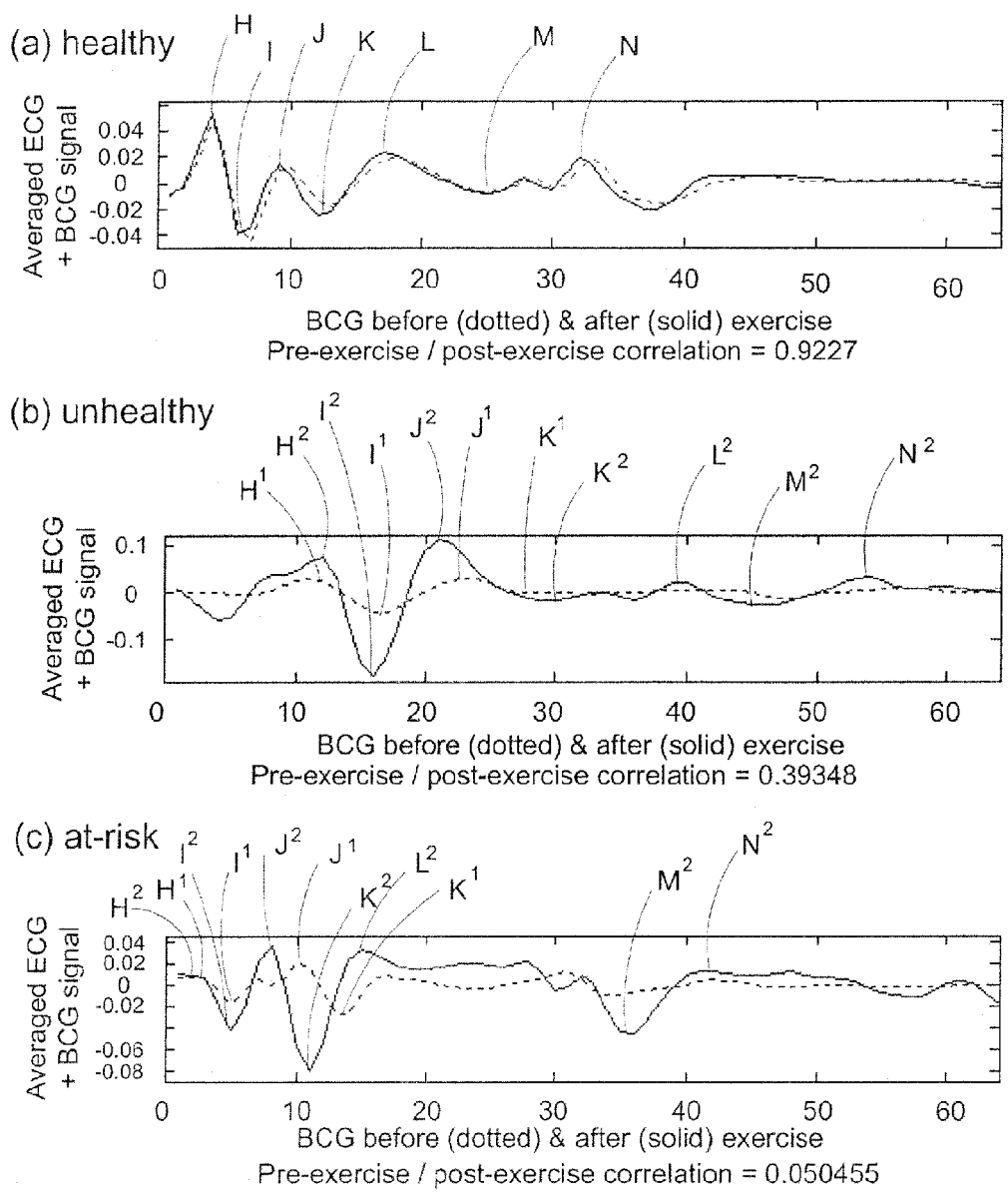

MONITORING PHYSIOLOGICAL CONDITION AND DETECTING ABNORMALITIES

CROSS-REFERENCE TO RELATED APPLICATIONS

This application is a continuation application of U.S. application Ser. No. 11/743,591, filed May 2, 2007, now U.S. Pat. No. 7,846,104; which claims the benefit of U.S. Provisional Application Ser. No. 60/888,930, filed Feb. 8, 2007; both of which are hereby incorporated by reference in their entireties.

FIELD OF THE INVENTION

This invention relates to monitoring cardiovascular health. More particularly, this invention relates to systems and methods for early detection of cardiovascular abnormalities and malfunctions.

BACKGROUND OF THE INVENTION

Numerous types of malfunctions and abnormalities that commonly occur in the cardiovascular system, if not diagnosed and appropriately treated or remedied, will progressively decrease the body's ability to supply sufficient oxygen to satisfy the coronary oxygen demand when the individual encounters stress. The progressive decline in the cardiovascular system's ability to supply oxygen under stress conditions will ultimately culminate in a heart attack, i.e., myocardial infarction event that is caused by the interruption of blood flow through the heart resulting in oxygen starvation of the heart muscle tissue (i.e., myocardium). In serious cases, the consequences are mortality while in less serious cases, permanent damage will occur to the cells comprising the myocardium that will subsequently predispose the individual's susceptibility to additional myocardial infarction events.

In addition to potential malfunctions and abnormalities associated with the heart muscle and valve tissues (e.g., hypertrophy), the decreased supply of blood flow and oxygen supply to the heart are often secondary symptoms of debilitation and/or deterioration of the blood now and supply system caused by physical and biochemical stresses. While some of these stresses are unavoidable, increasing age, heredity and ender, many of the causative factors of cardiovascular diseases and malfunction are manageable, modifiable and treatable if their debilitating effects on the cardiovascular system are detected early enough. Examples of such modifiable risk factors include high blood pressure, management of blood cholesterol levels. Diabetes mellitus, physical inactivity, obesity, stress, and smoking. Examples of cardiovascular diseases that are directly affected by these types of stresses include atherosclerosis, coronary artery disease, peripheral vascular disease and peripheral artery disease. In many patients, the first symptom of ischemic heart disease (IHD) is myocardial infarction or sudden death, with no preceding, chest pain as a warning.

Screening tests are of particular importance for patients with risk factors for IHD. The most common initial screening test for IHD is to measure the electrical activity over a period of time which is reproduced as a repeating wave pattern, commonly referred to as an electrocardiograph (ECG), showing the rhythmic depolarization and repolarization of the heart muscles. Analysis of the various waves and normal vectors of depolarization and repolarization yields important diagnostic information. However, ECG measurements are not particularly sensitive nor are the data very useful for detecting cardiovascular abnormalities or malfunctions. Therefore, stressing the heart under controlled conditions and measuring changes in the ECG data is usually, but not always, the next step. The stresses may be applied by the performance of physical exercise or alternatively, by administration of pharmaceutical compounds such as dobutamine, which mimic the physiological effects of exercise. Other screening tests for IHD include the radionucleotide stress test which involves injecting a radioactive isotope (typically thallium or cardiolyte) into a patient's bloodstream, then visualizing the spreading of the radionucleotide throughout the vascular system and its absorption into the heart musculature. The patient then undergoes a period of physical exercise after which, the imaging is repeated to visualize changes in distribution of the radionucleotide throughout the vascular system and the heart. Stress echocardiography involves ultrasound visualization of the heart before, during and after physical exercise. The radionucleotide stress test and stress echocardiography are often used in combination with ECG measurements in order to gain a clearer understanding of the state of individual's cardiovascular health.

However, there are a number of serious limitations associated with the use of ECG and related stress tests for detecting abnormalities and malfunctions that are indicators of ischemic heart disease. ECG printouts provide a static record of a patient's cardiovascular function at the time the testing was done, and may not reflect severe underlying heart problems at a time when the patient is not having any symptoms. The most common example of this is in a patient with a history of intermittent chest pain due to severe underlying coronary artery disease. This patient may have an entirely normal. ECG at a time when he is not experiencing any symptoms despite the presence of an underlying cardiac condition that normally would be reflected in the ECG. In such instances, the ECG as recorded during an exercise stress test may or may not reflect an underlying abnormality while the ECG taken at rest may be normal. Furthermore, many abnormal patterns on an ECG may be non-specific, meaning that they may be observed with a variety of different conditions. They may even be a normal variant and not reflect any abnormality at all. Routine exercise ECG is not recommended in patients who have no signs or symptoms of coronary artery disease. Exercise ECG is notoriously ineffective at predicting underlying coronary artery disease, and a positive exercise ECG test in an apparently healthy patient is not known to have any association with cardiovascular morbidity and mortality.

Ballistocardiography (BCG) is a non-invasive method of graphically recording minute movements on an individual's body surface as a consequence of the ballistic i.e., seismic forces associated with cardiac function, e.g., myocardial contractions and related subsequent ejections of blood, ventricular filling, acceleration, and deceleration of blood flow through the great vessels. These minute movements are amplified and translated by a pick-up device (e.g., an accelerometer) placed onto a patient's sternum, into signals with electrical potentials in the 1-20 Hz frequency range and recorded on moving chart paper. The rhythmic contractions of the heart and related flows of blood within and from. the heart's chambers under resting and stressed conditions produce repeating BCG wave patterns that enable visual detection and assessment by qualified diagnosticians of normal and abnormal cardiovascular function. The BCG records the vigor of cardiac: ejection and the speed of diastolic filling. It provides a practical means of studying the physiologic response of the heart in its adjustment to the stress of exercise. The application of the light BCG exercise test to subjects without clinical or ECG evidence of heart disease, or to hypertensive subjects, or to patients with coronary artery disease and to those suspected of having myocarditis, provides information of clinical importance which cannot be obtained from any other means of physical diagnosis or from the BCG at rest (Mandelbaum et al., 1954. Circulation 9:388-399). The most common BCG wave pattern classification system is known as the Starr system (Starr et al., 1961, Circulation 23: 714-732) and identifies four categories of cardiovascular function depending on the abnormalities in the measured BCG signals. In class 1, all BCG complexes are normal in contour. In class 2, the majority of the complexes are normal, but one or two of the smaller complexes of each respiratory cycle are abnormal in contour. In class 3, the majority of the complexes are abnormal in contour, usually only a few of the largest complexes of each respiratory cycle remaining normal and in class 4., there is such complete distortion that the waves cannot be identified with confidence, and the onset of ejection could not be located without the assistance of a simultaneous ECG (Starr, 1964, J. Am. Med. Assoc. 187:511). In general, a normal healthy person should belong to Starr class 1, and person belonging to class 3 or 4 has a significant abnormality in one or more components of the cardiovascular system. However, the classification is not exact, as it is done visually and depends on the person making the classification (Starr, 1964, J. Am. Med. Assoc. 187:511).

Coronary angiography enables visualization and assessment of potential cardiovascular abnormalities and malfunctions that are not possible to detect with the afore-mentioned stress tests, including as occlusions, stenosis, restenosis, thrombosis, aneurismal enlargement of coronary artery lumens, heart chamber size, heart muscle contraction performance and heart valve function. During a coronary angiogram, a small catheter is inserted through the skin into an artery in either the groin or the arm. Guided with the assistance of a fluoroscope, the catheter is then advanced to the opening of the coronary arteries, the blood vessels supplying blood to the heart. Next, a small amount of radiographic contrast solution is injected into each coronary artery. The images that are produced are called the angiogram. Although angiographic images accurately reveal the extent and severity of all coronary arterial blockages and details of the heart musculature, the procedure is invasive and requires the use of local anaesthesia and intravenous sedation.

SUMMARY OF THE INVENTION

The exemplary embodiments of the present invention, at least in some forms, provide systems, methods, devices, apparatus and software programs for acquiring, processing, synchronizing, storing and reporting at least two physiologically generated signals useful for monitoring the physiological condition of a mammalian system and for detecting abnormalities therein.

According to one exemplary embodiment, there is provided a system configured for monitoring the cardiovascular condition of a mammalian body. The system is provided with at least: (a) a plurality of devices configured to concurrently detect, acquire and transmit at least two different types of physiological signals produced by the cardiovascular system, (b) an analog-digital converter for converting the signals into digital data that can be processed and stored, (c) at least one apparatus configured to receive therethrough and condition the at least two signals, (d) a microprocessor suitably configured with hardware, an operating system and software provided for concurrently processing, analyzing, characterizing, reporting and transmitting said physiological and said conditioned signals, (e) a software program configured to concurrently process said conditioned signals to at least firstly detect repeating cyclical patterns in the conditioned signals, secondly to identify and characterize individual components comprising the repeating cycles, thirdly to identify a first reference component in at a first conditioned signal and a second reference signal in a second conditioned signal, fourthly to synchronize at least a first conditioned signal with a second conditioned signal by aligning the first and second reference points, and then subsequently aligning the repeating cyclical pattern of the first conditioned signal with the repeating cyclical pattern of the second conditioned signal in constant reference to the first and second reference points, and fifthly producing at least a synchronized paired signal derived therefrom, and (f) a database provided for communicating and cooperating with the microprocessor for storing therein and providing therefrom the physiological signals, conditioned signals, synchronized signals and signal outputs derived therefrom.

According to one aspect, there is provided a plurality of devices configured for concurrently detecting, acquiring and transmitting at least two physiological signals from a cardiovascular system. Exemplary suitable signals include electrical signals, electronic signals, seismic signals, mechanical signals, acoustic signals, imaging signals and the like. Suitable devices are exemplified by electrocardiographs, ballistocardiographs, seismocardiographs, angiographs and the like. Additional physiological monitoring equipment and instruments exemplified by pulsoximeters and blood pressure measuring devices, may be optionally provided to cooperate with said devices. The signals may be transmitted by wires or by wireless means.

According to another aspect, there is provided a filtering apparatus configured to remove extraneous noise components from the digital signals converted from the physiological signals acquired from the mammalian cardiovascular system thereby providing at least two conditioned signals.

According to exemplary embodiment of the present invention, there is provided at least one software program configured to concurrently perform a plurality of the following functions on the at least two conditioned signals: (a) process, (b) analyze, (c) optimize, (d) transform, (e) identify repeating cyclical patterns, (f) identify and characterize individual components of the repeating cyclical patterns, (g) identify a reference component in each of the cyclical patterns comprising each of the conditioned signals, (h) synchronize at least two of the conditioned signals by aligning the reference component of a first conditioned signal with the reference component of the second conditioned (i) generate output comprising at least one synchronized signal wave pattern, (j) report identifying and characterizing key components of the at least one synchronized signal wave pattern relating to a physiological condition, (k) store, and (k) re-transmit the synchronized signals. It is within the scope of this invention for the synchronized signals to be transmitted back to the mammalian system for providing a stimulatory signal thereto.

According to one aspect, the software program is suitably configured for processing, comparing and reporting a plurality of synchronized signals, and providing outputs therefrom.

According to another aspect, the software program may comprise a plurality of mathematical algorithms, or alternatively heuristic algorithms, or optionally, a combination of mathematical and heuristic algorithms.

According to another exemplary embodiment of the present invention, there is provided a database for storing therein and providing therefrom a plurality of synchronized signals produced as disclosed herein.

According to one aspect, the database may be provided as an integral component of the microprocessor provided herein.

According to another aspect, the database may be contained in a facility provided for such purposes. The database is configured receive therein pluralities of synchronized signals produced as disclosed herein. The synchronized signals may be delivered to and transmitted from the database base electrically, electronically, acoustically, via beams of light, and the like using wired or alternatively wireless transmission methods.

BRIEF DESCRIPTION OF THE DRAWINGS

The present invention will be described in conjunction with reference to the following drawing, in which:

FIG. 3 is a schematic diagram showing the relationships between the rhythm electrical functions and related physical motions of a physiologically normal heart cooperating with a physiologically normal cardiovascular system, with reference to: (a) electrocardiographic (ECG) events, (b) systolic and diastolic periods of time, (c) blood pressure during the systole and diastole periods, and (d) ballistocardiographic (BCG) events;

FIG. 12a shows a raw unconditioned and unsynchronized ECG-BCG signal set of a healthy individual with a well-functioning cardiovascular system, collected during a resting stage prior to exercising, while FIG. 12b shows a raw unconditioned and unsynchronized ECG-BCG signal set collected from the healthy individual during the post-exercise period.

FIG. 14a shows a raw unconditioned and unsynchronized ECG-BCG signal set of an unhealthy individual with a somewhat debilitated cardiovascular system, collected during a resting stage of prior to exercising, while

FIG. 16a shows a raw unconditioned and unsynchronized ECG-BCG signal set of an at-risk individual with a seriously debilitated cardiovascular system, collected during a resting stage prior to exercising, while

FIGS. 18a, 18b and 18c are comparisons of the overlaid synchronized pre- and post-exercise BCG signals for the healthy individual, unhealthy individual, and at-risk individual respectively.

DETAILED DESCRIPTION OF THE INVENTION

The present invention relates to the detection and monitoring of two disparate signals associated with rhythmic electrical cardiovascular functions and physical movements associated with the beating of an individual's heart, and the synchronization of a selected signal to the other signal whereby the synchronized signal enables and facilitates detection of potential abnormalities and malfunctions associated with the individual's cardiovascular system. Two exemplary suitable signals for monitoring cardiovascular function and for synchronization with each other are ECG and BCG signals. A brief description follows of cardiovascular functions as they relate to the generation of ECG and BCG signals, for reference to during disclosure herein of how either of these signals may be synchronized to the other for the detection of potential cardiovascular abnormalities and malfunctions according to the present invention.

Figure 1:
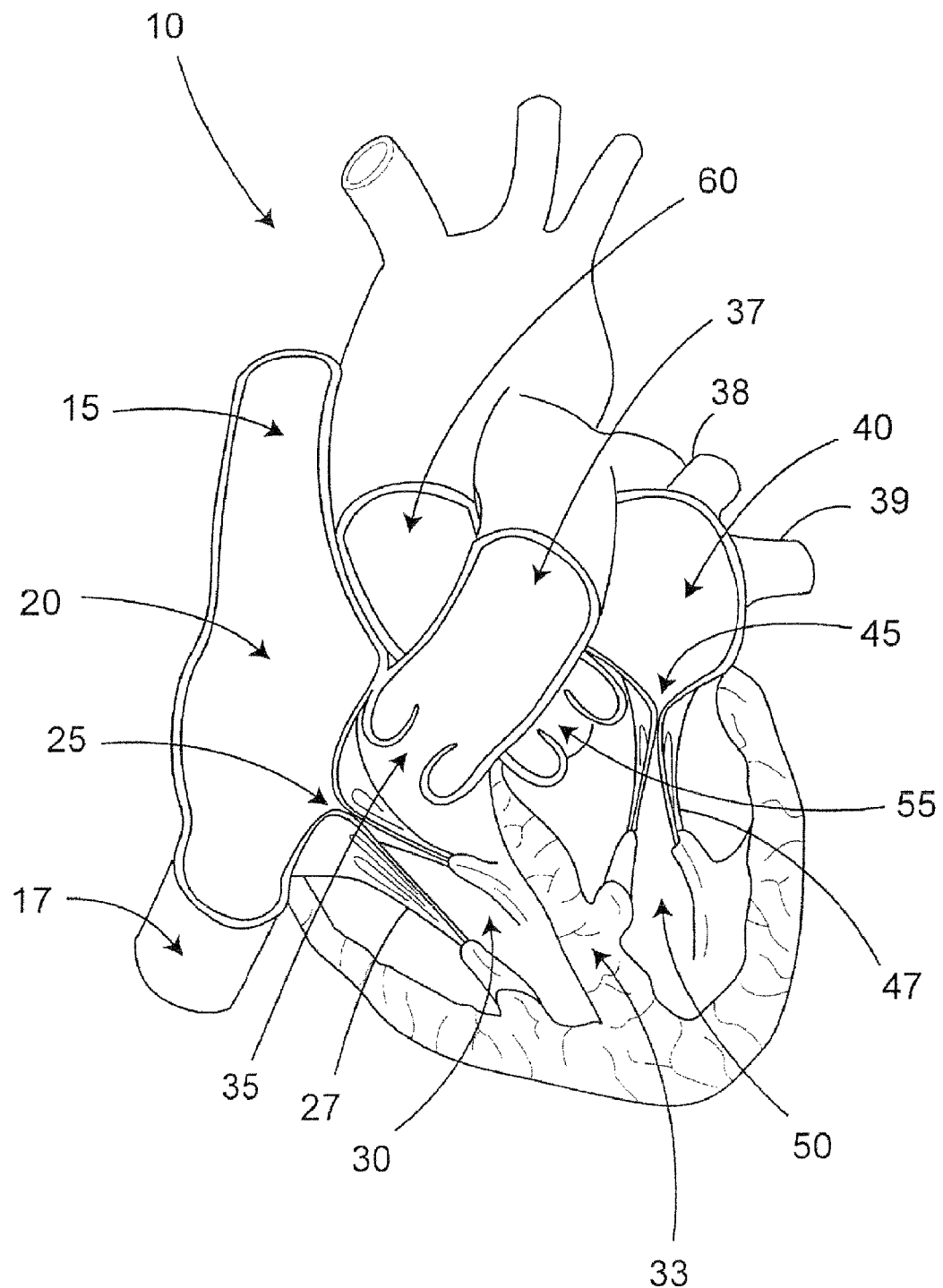
FIG. 1 is a cross-sectional perspective view of the heart showing the tricuspid and mitral valves in opened positions, and the pulmonary and aortic valves in closed positions.
Figure 2:
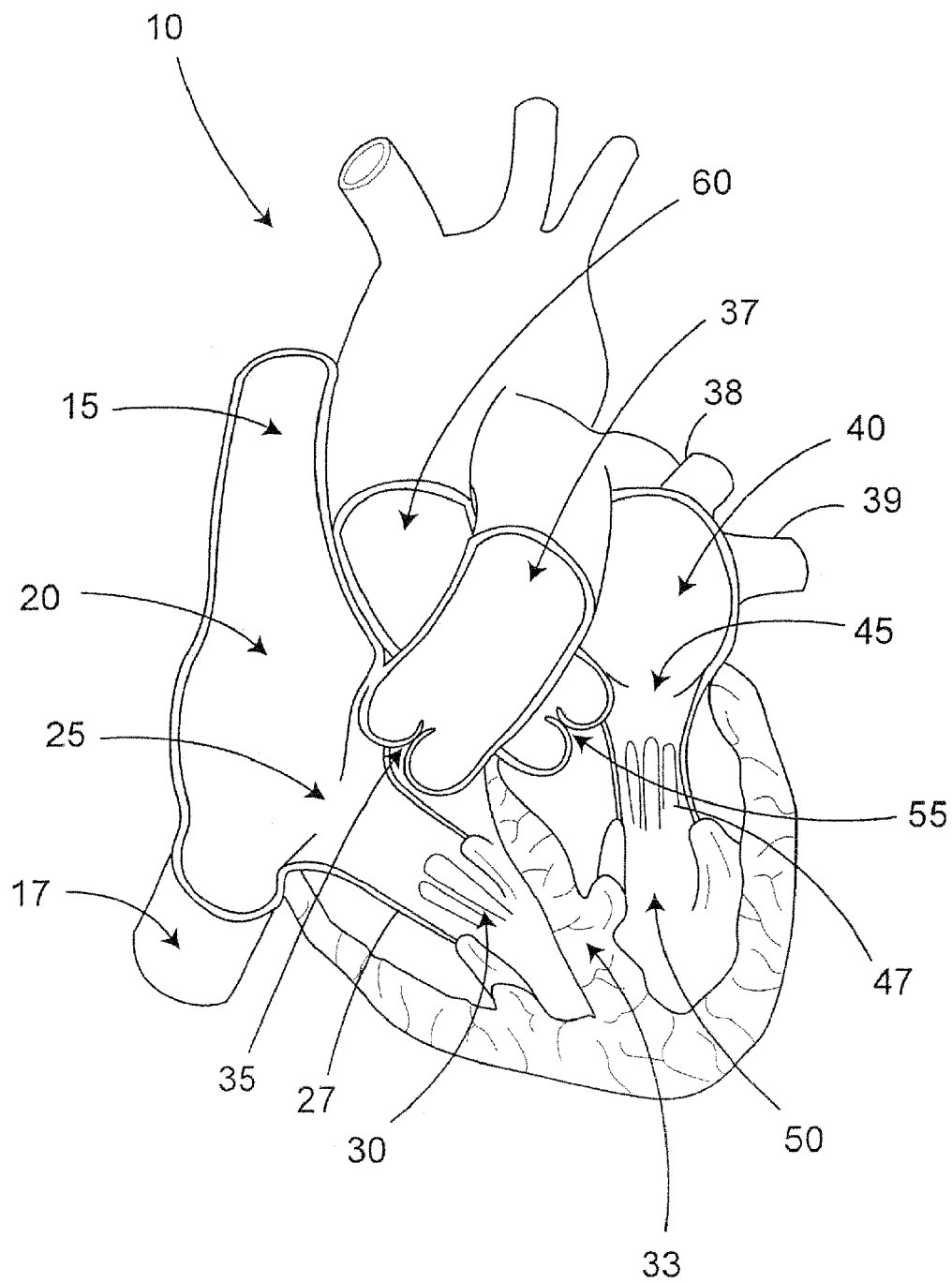
FIG. 2 is a cross-sectional perspective view of the heart showing the tricuspid and mitral valves in closed positions, and the pulmonary and aortic valves in opened positions.

As shown in FIGS. 1 and 2, the heart 10 comprises four chambers, the right atrium 20 interconnected with the right ventricle 30 by the tricuspid valve 35, and the left atrium 40 interconnected with the left ventricle 50 by the mitral valve 45. Blood is delivered into the right atrium 20 from the upper half of the body via the superior vena cava 15, and from the lower half of the body via the inferior vena cava 17. The tricuspid valve 25 is opened by concurrent contraction of the right atrium myocardium (i.e., muscle tissue) and the right ventricular papillary muscles 27 thereby allowing blood flow from the right atrium 20 into the right ventricle 30, and then closes when the papillary muscles 27 relax. When the myocardium of the right ventricle 30 contracts, blood is forced from the right ventricle 30 through the pulmonary valve 35 into the pulmonary artery 37 which delivers the blood into the lungs wherein it is oxygenated. The oxygenated blood is then returned into the left atrium via pulmonary veins 38 and 39. The oxygenated blood flows from the left atrium into the left ventricle when the mitral valve 45 is opened by concurrent contraction of the left atrium myocardium and the left ventricular papillary muscles 47 thereby allowing blood flow from the left atrium 40 into the left ventricle 50, and then closed when the papillary muscles 47 relax. The oxygenated blood is then forced oat of the left ventricle 50 through the aortic valve 55 into the aorta which delivers the oxygenated blood to throughout the body via the peripheral vascular system.

Every rhythmic 'beat' of the heart involves three major stages: atrial systole, ventricular systole and complete cardiac diastole. Electrical systole is the electrical activity that stimulates the muscle tissue, i.e., the myocardium of the chambers of the heart to make them contract. Referring to FIG. 3(b), atrial systole 110 is the period of contraction of the heart muscles (i.e., myocardia) encompassing the right and left atria 20 and 40. Both atria 20 and 40 contract concurrently with papillary muscle 27 and 47 contraction thereby forcing open the tricuspid valve 25 and the mitral valve 45 as shown in FIG. 1. Electrical systole, i.e. electrical depolarization of the atria 20 and 40 begins within the sinoatrial (SA) node located in the right atrium just below the opening to the superior vena cava. The conduction electrical depolarization continues to travel in a wave downwards, leftwards and posteriorly through both atria depolarising each atrial muscle cell in turn. It is this propagation of charge that can be seen as the P wave on an ECG as exemplified in FIG. 3(a). This is closely followed by mechanical systole i.e., mechanical contraction of the atria which is detected on a BCG (FIG. 3(d)) as an impact (i.e., "h" peak) and recoil (i.e., "i" valley) wave pattern. As the right and left atria 20 and 40 begin to contract, there is an initial high velocity flow of blood into the right and left ventricles 30 and 50 detectable as the "j" peak on the BCG (FIG. 3(d)). Continuing atrial contraction as the tricuspid valve 25 begins to close forces an additional lower velocity flow of blood into the right and left ventricles 30 and 50. The additional flow of blood is called the "atrial kick" and is shown in FIG. 3(d) as the "a-a$^1$" wave pattern. After the atria are emptied, the tricuspid and mitral valves 25 and 45 close thereby giving rise to the footward "g" wave pattern on the BCG as shown in FIG. 3(d).

Referring to FIG. 3(b), ventricular systole 120 is the contraction of the muscles i.e., myocardia of the left and right ventricles 30 and 50, and is caused the electrical depolarization of the ventricular myocardia giving rise to the QRS complex in a ECG plot as shown in FIG. 3(a). The downward Q wave is caused by the downward flow of depolarisation through the septum 33 along a specialized group of cells called "the bundle of His". The R wave is caused by depolarization of the ventricular muscle tissue, while S wave is produced by depolarization of the heart tissue between the atria 20 and 40 and ventricles 30 and 50. As the depolarization travels down the septum and throughout the ventricular myocardia, the atria 20 and 40 and sinoatrial node start to polarise. The closing of the tricuspid and mitral valves 25 and 45 mark the beginning of ventricular systole and cause the first part of the "lub-dub" sound made by the heart as it beats. Formally. this sound is known as the "First Heart Tone" and is produced during the period of time shown in FIG. 3(h) as S$_1$. As the electrical depolarization of the ventricular myocardia peaks, as exemplified by the "R" peak shown in FIG. 3(a), the AV septum 33 separating the right and left ventricles 30 and 50 contracts causing an impact, i.e., the "H" peak and a recoil i.e., the "I" valley detectable on a BCG as shown in FIG. 3(d). The ventricular contraction forces the blood from the right ventricle 30 into the pulmonary artery 37 through the pulmonary valve 35, and from the left ventricle 50 into the aorta 60 through the aortic valve 55 under very high velocity thereby causing the "J" wave in the BCG as shown in FIG. 3(d). The deceleration of blood flow from the left ventricle 50 into the aorta 60 causes a footward decline in the BCG resulting in the "K" wave (FIG. 3(d). As the left ventricle 50 empties, its pressure falls below the pressure in the aorta 60, and the aortic valve 55 closes. Similarly, as the pressure in the right ventricle 30 falls below the pressure in the pulmonary artery 37, the pulmonary valve 35 closes. The second part of the "lub-dub" sound, i.e., the "Second Heart Tone" is produced during the period of time shown in FIG. 3(b) as S$_2$ and is caused by the closure of the pulmonary and aortic valves 35 and 55 at the end of ventricular systole thereby giving rise to the headward "L" wave detectable on a BCG as shown in FIG. 3(d.) Concurrently with the closing of the pulmonary and aortic valves 35 and 55, the AV septum 33 relaxes and moves headward, and the ventricular myocardia is re-polarized giving rise to the "T" wave in the corresponding ECG as shown in FIG. 3(a).

Cardiac diastole is the period of time when the heart 10 relaxes after contraction in preparation for refilling with circulating blood. Atrial diastole is when the right and left atria 20 and 40 are relaxing, while ventricular diastole is when the right and left ventricles 30 and 50 are relaxing. Together, they arc known as complete cardiac diastole 150 as shown in FIG. 3(b). During the period of atrial diastole, the right atrium 20 is re-filled by deoxygenated blood returning from the upper half of the body via the superior vena cava 15 and from the lower half of the body via the inferior vena cava 17, while the left atrium is re-filled with oxygenated blood returning from the lungs via pulmonary veins 38 and 39. Re-filling of the atria 20 and 40 causes a downward "M" wave in the BCG FIG. 3(d) early in diastole which coincides with repolarization of the bundle of His cells, which is shown as the "U" wave in FIG. 3(a). As the right and left atria 20 and 40 are filled to their maximum capacities, the reflux of blood against the tricuspid valve 25 and mitral valve 45 cause an upward "N" wave in the BCG shown in FIG. 3(d).

In summary, an ECG, as exemplified in FIG. 3(a) provides information on the rhythmic formation, propagation and regeneration of electrical signals within the heart muscles wherein: (a) the P wave results from electrical depolarization of the right and left atria signaling the onset of atrial systole during which time the right and left atria contract, (b) the QRS wave pattern results from depolarization of the right and left ventricles signaling the onset of ventricular systole during which time the right and left ventricles contract, (c) the subsequent T wave is produced by electrical repolarization of the ventricular myocardia, and (d) the U wave is produced by electrical repolarization of the bundle of His cells. The T and U waves are notoriously hard to locate and annotate due to their slow slopes and low amplitudes.

The BCG, as exemplified in FIG. 3(d), records the vigor of cardiac ejection of blood from the atria and ventricles, and the speed of filling of the atrial chambers during the diastolic period. More specifically, the BCG provides information on the mechanical functioning and related physical movements of the heart muscles, valves, and related flows of blood into, between and out of the atria and ventricles as a consequence of electrical depolarization and re-polarization of the heart tissues. As the heart pumps blood from the right and left atria via the right and left ventricles into the pulmonary artery and the aorta, and as the blood flow returns to the left and right atria, recoil pressures in the opposite directions are applied by the body. The pumping pressures result in headward BCG wave peaks, while the recoil pressures on blood flow result in the downward BCG wave peaks. The "h-i" wave component of the BCG shows the physical impact and recoil from depolarization of the SA node and related atrial movements. The "j-a-a'" wave pattern records the impact and recoil of the heart in response to blood flow from the atria 20 and 40 into the right and left ventricles 30 and 50. The "g" wave pattern is a caused by the closing of the tricuspid and mitral valves 35 and 45. The "H-I" wave pattern is caused by the impact and recoil of the septum 33 and corresponds to the isometric phase of ventricular systole during which time the heart is physically twisting and moving upward within the chest cavity. The "J-K" wave pattern is caused by the initial highly forceful impact of blood from the right and left ventricles into the pulmonary and aortic arteries (the J peak) followed by deceleration of blood flow in the aorta (the j-K slope). The L wave is caused by the movement of the septum during isometric relaxation, while the M wave is caused by the flow of blood into the right atrium from the vena cava vessels and into the left atrium by the pulmonary veins. The heart is physically recoiling and moving downward in the chest cavity during isometric relaxation. The N wave is caused by impact of blood onto the ventricular myocardia at the end of early diastolic filling due to reflux.

Considerable energy is generated by the ventricular myocardia during ventricular systole, and the strength of ventricular contraction is fueled by the oxygen in the blood returning from the lungs into the left ventricle via the left atrium. About 80% of the oxygen in the blood flowing through the left ventricle is removed to supply the ventricular myocardial oxygen demand during ventricular systole. The cardiovascular systems of most individuals under "resting" conditions, can supply adequate amounts of oxygen during coronary perfusion to provide regular repeating ECG and BCG patterns as exemplified in FIGS. 3(a) and 3(d). When healthy individuals are placed under stressed conditions, e.g., exercise, it is known that as the heart rate increases to provide sufficient oxygen to the maintain efficient cardiovascular function while supplying additional oxygen to meet the demands from the peripheral musculature, the related ECG and BCG wave patterns reproduce the typical repeating wave patterns as illustrated in FIGS. 3(a) and 3(d) but the slopes and amplitudes of the wave patterns increase significantly. However, individuals experiencing some debilitation in their cardiovascular physiology and function, when stressed, tend to produce BCG signals that show significant variations in their repeating BCG wave patterns when compared to their BCG produced under "resting" conditions. FIGS. 4(a)-4(d) show four types of exemplary BCG signals that are divided into separate classes of cardiovascular abnormalities based on the Starr classification system (Starr, 1964, Journal of the American Medical Association 187: 511). In Class 1 (FIG. 4(a)), all BCG wave patterns are normal in contour. In Class 2 (FIG. 4(b)), the majority of the BCG wave patterns are normal but one or two of the smaller wave patterns in each respiratory cycle are abnormal. In Class 3 (FIG. 4(c)), the majority of the BCG wave patterns are abnormal in contour and usually, only a few of the largest wave patterns of each respiratory cycle remain normal. Lastly, in Class 4 (FIG. 4(d)), there is such complete distortion in the BCG wave patterns that none of the waves can be identified with confidence, and it is difficult to determine the onset of each rhythmic cycle. In general, a normal healthy person should belong to the Starr Class 1 (FIG. 4(a)), while a person producing BCG wave patterns that fall into the Starr Classed 3 or 4 (FIG. 4(c)) or 4(d)) has significant cardiovascular abnormalities and/or malfunctions.

We have surprisingly discovered that, regardless of the type of BCG wave pattern produced by an individual under stressed conditions in reference to the Starr classification system, it is possible to synchronize the individual's rhythmic BCG pattern. with their ECG signal under non-stressed, i.e., resting stage conditions, and then characterize the individual's cardiac function by calculating a plurality of the following parameters:
  (1) stroke volume: the amount of blood ejected from the left ventricle during systole. Stroke volume (SV)=end diastolic volume (EDV)−end systolic volume (ESV);
  (2) cardiac output: the volume of blood pumped by the left ventricle per minute, calculated by multiplying the stroke volume by the number of heart beats per minute. Cardiac output (CO)=SV×heart rate (HR measured in beats per minute);
  (3) ending diastolic volume: the volume of blood contained in the left ventricle at the end of the rest phase when the left ventricle is at its fullest;
  (4) ending systolic volume: the volume of blood left in the left ventricle at the end of the systolic period when the ventricle contains its lowest volume;
  (5) ventricular ejection fraction: the percentage of the ending diastolic volume that is ejected during each heart beat. Ejection fraction (EF)=SV/EDV;
  (6) cardiac output index: the volume of blood pumped by the left ventricle per minute normalized to the body surface area (measured in meters$^2$). Cardiac output index (CI)=CO÷body surface area (BSA)=SV×HR/BSA;
  (7) Pre-ejection period: The time from the Q-wave peak on the ECG to the opening of the aortic valve;
  (8) Cardiac performance index (CPI) (isovolumetric relaxation time+isovolumetric contraction time)/Ejection time (ET). The CPI can also be calculated as the (time period between the 1-peak and the L-peak) ET, The CPI can also be calculated as the (time period between aortic valve opened and aortic valve closed)/(time period between the I-peak and the L-peak).

The quantifications of the above parameters are dependent on synchronizing, as illustrated in FIGS. 3(a) and 3(d), the R wave peak on an ECG caused by the depolarization of the ventricular muscle tissue with the H peak on a corresponding BCG which signals the rapid increase in intraventricular pressure caused by the impact of the septum as the direct consequence of the depolarization of the ventricular muscle pressure. Since the H-wave and I-wave on a BCG are caused by the impact and recoil of the septum concurrent with depolarization of the ventricular muscle tissue, (a) the time duration of the H-I wave, i.e., the isovolumetric contraction time, and (b) the distance between the H and I peaks over the duration of that wave, can be measured. These data enable calculation of the slope of the H-I wave and the time to maximum velocity of the blood flow resulting from the ventricular contraction which results in rapid blood flow into the aorta thereby causing the J-peak. The subsiding blood flow into the aorta from ventricle results in the K-Peak. Since most individuals at resting stage, reproduce all of the H-I-J-K-L-M-N peaks of a "normal"-looking BCG pattern, the synchronized H-peak, and the detected I-peak and J-peaks can be used to sequentially find and mark the remaining K-L-M-N peaks. Marking each of these peaks enables precise calculation of the slope, the slope, the J-K slope, the K-L slope, the L-M slope, and the M-N slope. These data enable calculations of the time to maximum velocity for each slope thereby enabling calculation of the volumes of blood flow, and the positive and negative pressure values that are exerted on and by the various heart muscles and valves, Furthermore, it is also possible to back-calculate from the synchronized H-peak and precisely mark the preceding g-a$^1$-a-j-i-h wave patterns.

Figure 4:
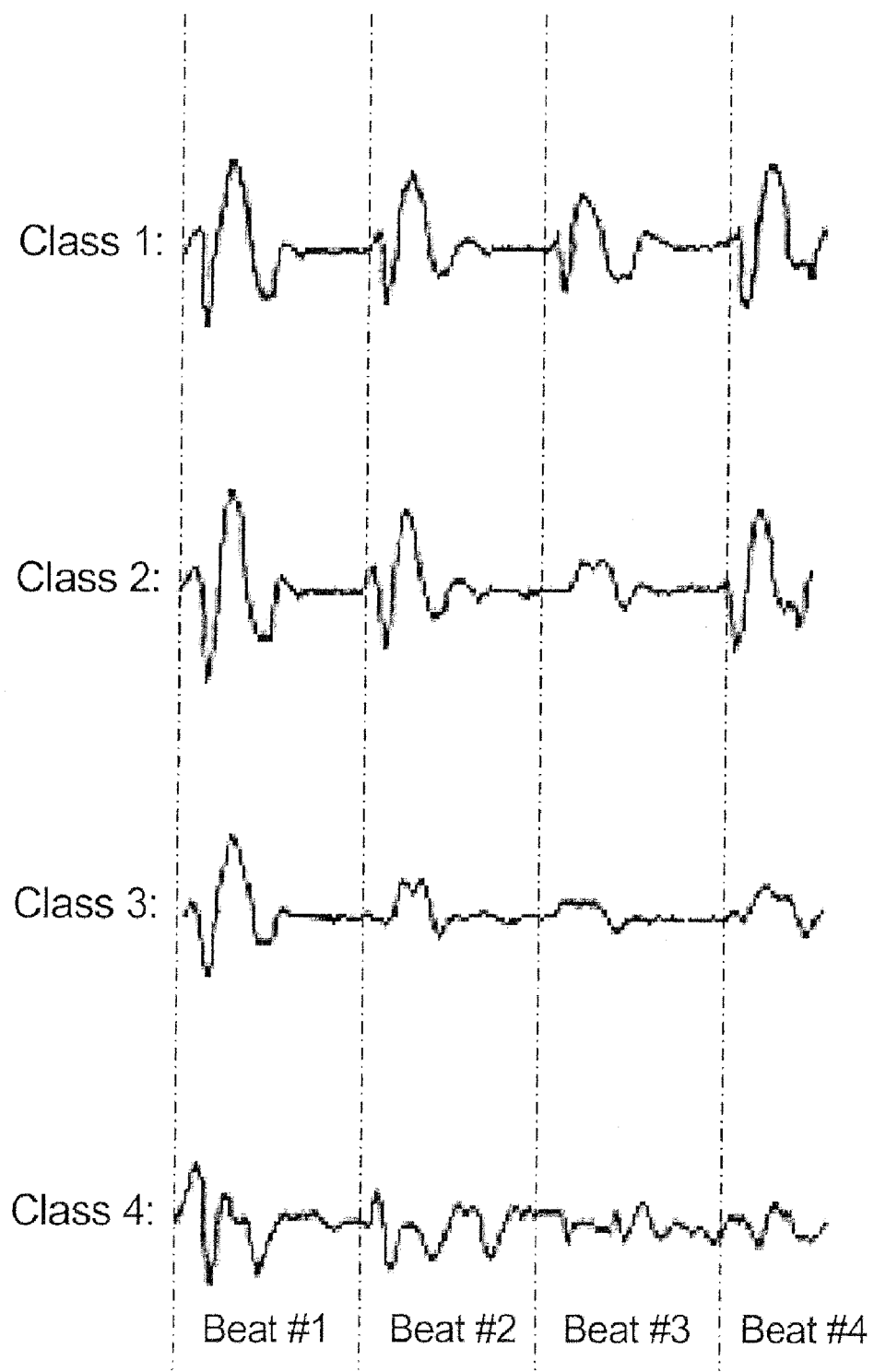
FIG. 4 is an exemplary chart showing the traditional Starr BCG signal classification system.

When individuals with healthy cardiovascular systems, i.e., those within the Starr Class 1 range, are stressed such that their heart rates increase significantly to supply adequate oxygen in the blood stream throughout the body, the slopes of their H-I and J-K wave patterns will increase in height, have steeper slopes and have shorter time period, while the L-M-N waves will repeat distinctly, regularly and their slopes often become steeper. However, individuals with cardiovascular abnormalities and malfunctions, when stressed, will produce H-I and J-K slopes that are decreased in height and become longer, i.e., flatter, while L-M-N peaks tend to flatten out as shown in FIGS. 4(b) and 4(c). In cases where the severity of the cardiovascular abnormalities and malfunctions are increased, the heights of the H, J, L, and N peaks are significantly reduced to the point where the H-I, I-J, J-K, K-L, L-M and M-N slopes are similarly elongated and irregular as shown in FIG. 4(c). Table 1 shows a summary of various types of cardiovascular abnormalities and their effects on ECG and BCG wave patterns.

TABLE 1

| Cardiovascular abnormality | ECG Wave Patterns | BCG Wave Patterns |
|---|---|---|
| Ischemic Heart Diseases (IHD) | hyperacute T wave (tall T wave) ST segment Changes. T wave inversion. Q wave longer than 0.04 sec. S in V1 and V2 + R inV5 R in I + S inIII >25 mm | increased amplitude in K, J, L, M peaks broad K wave fused H-J wave patterns expiration. notched J waves changes in Q-I, Q-J, I-J slopes |
| Sinus Arrhythmia: tachycardia bradycardia | typical ECG wave patterns relating to heart rate, P wave or QRS wave patterns | prolonged H-I-J wave pattern often appears as Starr Class 3 or 4 wave patterns |
| Nonsinus Arrhythmia: ventricular & atrial flutter/fibrillation | ECG shows variable different P-QRS wave patterns | primarily produce Starr Class 3 or 4 wave patterns |
| Hypertension | variable ECG wave patterns. T inversions large S or R peaks. some ECG fluctuations similar to those for IHD | tall L wave. large H wave. H wave fused into the J wave |

We have discovered that the H-I-J-K-L-M-N wave peak data collected and calculated from the synchronized BCG and ECD signals under resting conditions, can be used as reference points to detect and identify different types of potential cardiovascular abnormalities by the changes that occur in one or more of the H-I, I-J, J-K, K-L, and M-N slopes when the individual is placed under stressed conditions. It is important to note that regardless of whether an individual is under resting or stressed conditions, synchronization of the H-peak on the BCG with the R-peak on the ECG during resting conditions will enable during stressed conditions, the precise marking of where the H-peak should occur on the BCG from the R-peak on the ECG. It is then possible to mathematically determine where the subsequent I-J-K-L-M-N peaks should have occurred. By referencing the synchronized h-i-j-a-$a^1$-g-H-I-J-K-L-M-N and wave peaks and H-I, I-J, J-K, K-L, L-M, M-N slopes produced by the individual under resting conditions, it is possible to identify and characterize the changes in the physical movements of the heart muscles and valves, and in the rates and patterns of blood flow into, through and out of the heart under stressed conditions. For example, significant decreases in the H and J peaks accompanied by elongation of the H-I and J-K slopes under stress conditions indicate that there is (a) a reduction in the rate of increase in intraventricular pressure in response to depolarization of the ventricular muscle pressure, i.e., there is less ventricular contractive force being generated during ventricular systole, which results in (b) less ejective force exerted on blood flow during ventricular contraction thereby resulting in a smaller J peak. The reduction in the H and J peaks is primarily as a consequence of insufficient oxygen delivery to the heart muscles in the blood returning from the lungs to the left atrium to supply the energy required for contraction of the left ventricle. Prolonged insufficient supply of oxygenated blood to the left ventricle will result in the decreases in the H and J peaks becoming more pronounced while the H-I and J-K slopes become more elongated. Individuals with severely reduced cardiovascular function will have significantly increased heart rates under stress, which can be detected by a significantly reduced time span between the $S_1$ and $S_2$ periods, i.e. the time period between the I peak signaling septum recoil during ventricular contraction and the L peak signally ventricular relaxation during which time the aortic valve is closed by backflow of blood ejected from the left ventricle. Malfunctioning in the aortic valve, e.g., incomplete closure or leakiness by the aortic valve results in a greater impact on the left ventricular wall during the early period of diastole and causes a larger spike, i.e. height in the N peak. Reduction in the height of the j peak and an elongation of the j-a slope under stressed conditions indicates that the right and left atria are contracting with less force compared to the resting stage, while disappearance of the $a^1$ peak indicates that the right atrium is not delivering the same pressurized volume of blood into the right ventricle for subsequent delivery into the pulmonary artery for transport to the lungs. A reduction or disappearance in the g wave indicates malfunction or abnormalities in closure of the tricuspid and/or mitral valves resulting in backflow leakage from the right and left ventricles into the right and left atria. When an individual with a malfunctioning and/or abnormal cardiosystem is relieved from the stressed conditions and returns to a resting stage, their ECG and BCG patterns return to the normal patterns previously recorded before the onset of the stress.

Figure 5:
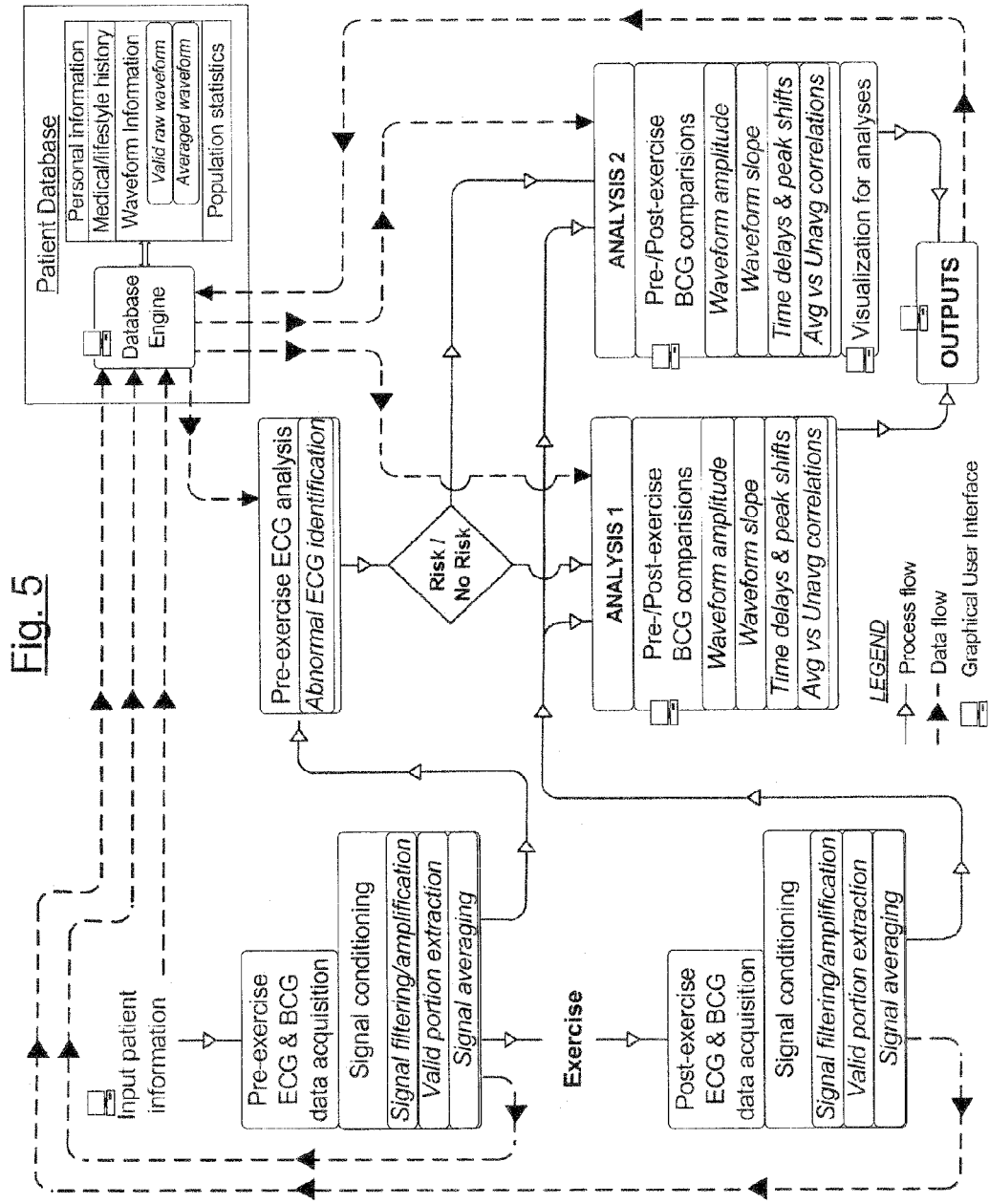
FIG. 5 is a schematic diagram showing an exemplary system of the present invention configured for concurrently detecting and transmitting ECG and BCG signals produced by a heart to a device configured to synchronize one of the signals and provide a visual output of the synchronized ECG and BCG signals.

An exemplary embodiment of the present invention for monitoring the physiological condition of the cardiovascular system and detecting abnormalities is shown in FIG. 5 and generally comprises at least: (1) one device configured for detecting electrical depolarization and re-polarization of an individual's heart tissues and for transmitting such information as a ECG signal, (2) one device configured for detecting physical movements on and/or within the individual's heart and related movements on their body surfaces and for transmitting such information as a BCG signal, (3) a device configured for receiving the ECG and BCG signals and conditioning at least one of the signals, (4) an analog-digital converter for converting the signals into digital data that can be processed and stored, (5) a microprocessor for computing, analyzing, reporting, transmitting and storing the digital data, (6) a computer software program comprising at least one algorithm configured for analyzing the ECG and BCG signals to: (a) detect the P-QRS peaks in an ECG signal, (b) detect and mark the H-I-J peaks in a BCG, (c) synchronize the H peak of the BCG signal with the R peak of the ECG signal, and (d) provide synchronized ECG and BCG signal outputs, and (7) a graphical user interface (GUI) program written in C++ language.

The system of the present invention may be suitably provided with a pulseoximeter configured to concurrently detect at least the amount of oxygen in the individual's blood and changes in the blood volume in their skin and transmit these data one of the device configured for receiving the ECG and BCG data or alternatively, to the microprocessor. The pulseoximeter may be optionally configured to detect and transmit the individual's heart rate. The system of the present invention may be optionally provided with a device configured to detect sounds made by the heart during its rhythmic systole-diastole periods and to transmit a phonocardiogram signal to the signal conditioning device. The system of the present invention may be optionally provided with a device configured to provide images of the heart during its rhythmic systole-diastole periods and to transmit an echocardiogram signal to the signal conditioning device. The computer program may optionally comprise a plurality of cooperating algorithms.

The device configured for receiving the ECG and BCG signals and the analog-digital converter may comprise a suitably configured motherboard provided with suitable electronic devices known to those skilled in these arts. The motherboard may be additionally provided with a microprocessor configured for receiving and running the software program comprising one or more mathematical algorithms and/or heuristic algorithms to at least separately process, analyze and synchronize the R peaks and H peaks of the concurrently received ECG and BCG signals and to provide an output comprising at least synchronized ECG-BCG wave-pattern signals. The computer software program may be suitably provided with an additional or optionally, a plurality of algorithms configured to heuristically separately process, analyze and synchronize the concurrently received ECG and BCG signals, and then to heuristically identify and mark the h-i-j-a-a$^1$-g and I-J-K-L-M-N peaks on the synchronized BCG signal. The computer software program may be suitably provided with at least one addition algorithm or optionally, a plurality of algorithms configured to process, compare, and analyze pluralities of synchronized ECG and BCG signals and to provide outputs relating to the similarities and differences among and between the pluralities of synchronized ECG and BCG signals.

Figure 6:
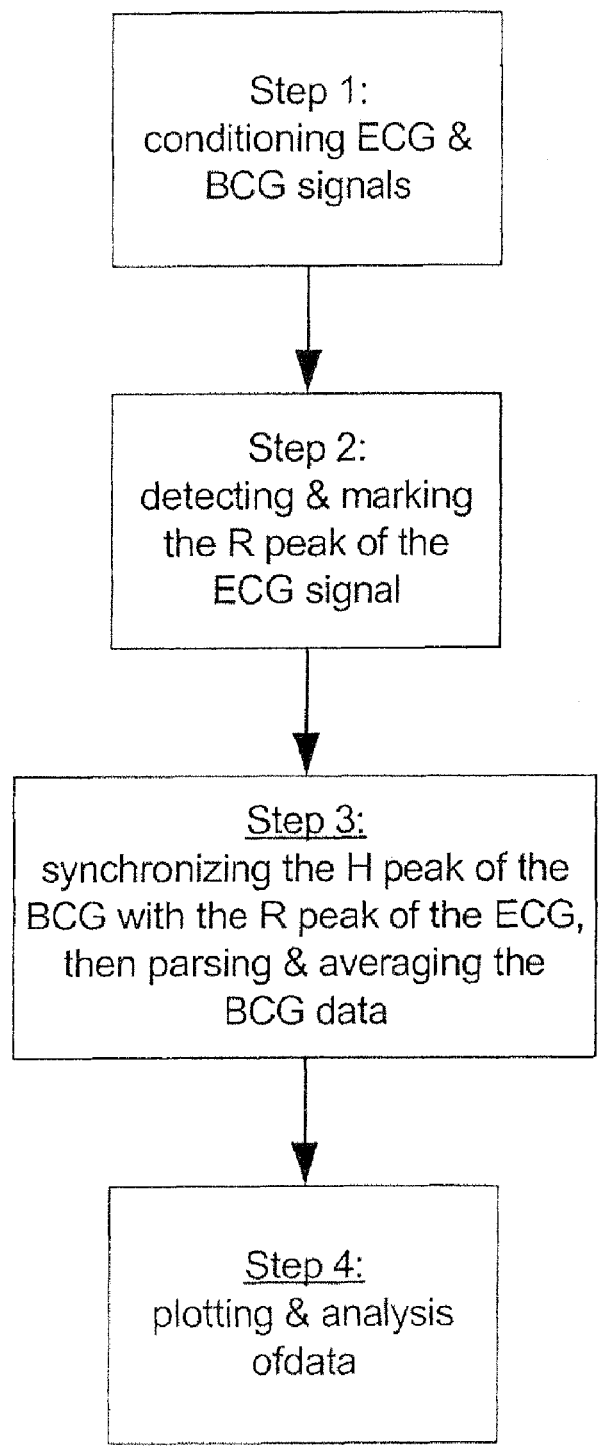
FIG. 6 is an flow chart of one embodiment of the present invention showing an exemplary method for processing and synchronizing concurrently produced ECG and BCG signals.
Figure 7:
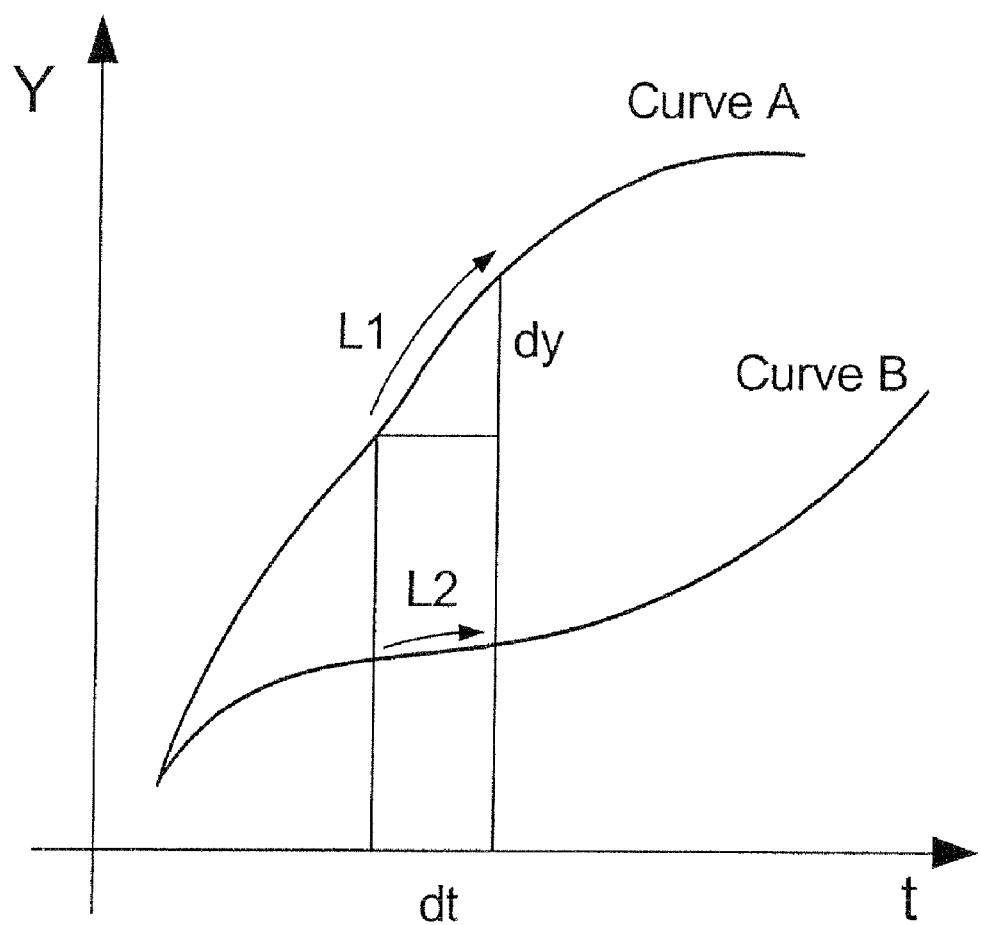
FIG. 7 is a graph illustrating a prior art curve-length concept.

FIG. 6 shows an exemplary 4-step flowchart according to one embodiment of the present invention, for processing and synchronizing concurrently produced ECG and BCG signals. The first step comprises conditioning of concurrently produced ECG and BCG signals to remove extraneous noise components thereby providing signal outputs that are transmitted with minimum relative loss or maximum relative gain. A suitable method for conditioning ECG and BCG signals is to pass each signal separately through fifth-order Butterworth filters wherein: (a) for the ECG signal, the high-pass cutoff frequency is set at about 40 Hz and the low-pass filter is set at about 1 Hz, and (b) for the BCG signal, high-pass cutoff frequency is set at about 25 Hz and the low-pass filter is set at about 1 Hz. The second step is to detect the R wave in the filtered ECG signal with an algorithm. A suitable algorithm may be developed by exploiting the curve-length concept which, in reference to FIG. 7, illustrates how the lengths L1 and L2 are able to characterize the shape of the curves, given a certain time interval DT. This principle can be applied to detect the wave fronts that characterize the beginning and the end of an episode arc-length relative to the i-th sample with the chord length, obtaining:

$$L = \sum_{i=0}^{x-1} l_i = \sum_{i=0}^{x-1} \sqrt{Tx^2 + (y_i - y_{i-1})^2} . \tag{1}$$

L is the total estimated length of the episode, Tx is the sampling interval, yi–yi–1 represents the i-th increment and n is a rough estimate of the duration of the episode (or waveform) to be detected: in this case n is an estimate of QRS duration. L can also be written:

$$L = Tx \cdot \sum_{i=0}^{x-1} \sqrt{1 + \frac{(y_i - y_{i-1})^2}{Tx^2}} = Tx \cdot \sum_{i=0}^{x-1} \sqrt{1 + \frac{Dy^2}{Tx^2}} \tag{2}$$

Finally, centering the computational window on the i-th sample and calling w=n/2, a recursive low computational cost form is obtained that may be incorporated in to computer software programs using assembly languages for DSPs processors known to those skilled in these arts:

$$U3_i = U3_{i-1} - (y_{i-w-2} - y_{i-w})^2 + (y_{i+w-2} - y_{i+w})^2 \tag{3}$$

The third step is to identify the H peak from the conditioned BCG signal, then synchronize the H peak with the R peak from the ECG signal, after with the conditioned BCG signal is parsed to locate and mark the h-i-j-a-a$^1$-g and I-J-K-L-M-N peaks, and then, average the conditioned BCG signal.

Suitable heuristic algorithms for (a) synchronizing the H peak with the R peak, then (b) parsing the conditioned BCG signal is parsed to locate and mark the h-i-j-a-a$^1$-g and I-J-K-L-M-N peaks, and then, (c) averaging the conditioned BCG signal, may be developed by using the ECG's R peaks as the synchronization points for the cycle-by-cycle length determination. Each cycle length is than divided into intervals according to the sample rate of the signals. The number of the intervals can be programmed and experimentally determined. An example is 2500 samples equivalent to 1.2 seconds of the acquired signal. The assigned intervals allow the signal processing. The segment points are than associated with the ECG pick values, when possible and as the additional synchronization option. The segmented signal is used for maxima and minima determination followed by the BCG's letter assignments. Each segment can be searched for a local minimum or maximum. The number of segments and their programmed assignments permit on a practical adjustments and experimental set-ups accordingly to the subject group and analysis requirements.

The assignments generally follow the steps listed below for the segmented ECG and BCG signals:
  1. first segment in BCG signal after R pick or the segment with the R pick is searched for a local maximum which determines H value of the BCG signal, 2. next local minimum of BCG signal segments (following H) is found for the assignment of I value of BCG
3. from I value the next segments are searched for the local maximum and J assignment, the next local minimum can be K pick of BCG signal,
4. synchronize and associate the segments and values to the ECG signal,
5. next local maximum of the ECG signal which follows J maximum (BCH signal) is T pick, the identification of the T permits on the re-synchronization of the segments,
6. the search of the segments following T pick determines the L (local maximum) and M (the local minimum),
7. the next assignment after L and M is the result of the search of the next local. maximum which becomes N pick of the BCG signal,
8. the segmentation permits on the time interval determination and the back calculation of the time related to the specific events (pick values),
9. the assignments are repeated for each next cycle of BCG signal as determined by R pick synchronization reference, after which, the cycle-by-cycle assignments can be averaged or considered separately.

The fourth step is to producing synchronized and marked outputs of the ECG and BCG signals, and transmitting the outputs to at least one electronic processing device, one data storage device and one visual output device. Exemplary suitable visual output devices include display monitors, printers and plotters. The data produced by the individual as described will serve as the resting-stage reference points for subsequent physiological stress testing outputs, as will be described in more detail below.

Another embodiment of the present invention comprises detecting, transmitting, conditioning, synchronization, and processing of a plurality of signals produced by an individual's cardiovascular system during resting stage conditions, and storing the digital data developed therefrom in a data storage device. Suitable signals are ECG signals and BCG signals. The signals may optionally, or additionally, comprise phonocardiogram and/or echocardiogram signals. While remaining connected to the system of the present invention, the individual is then placed under stressed conditions for real-time ongoing detection, transmission, conditioning, synchronization and processing of the signals output by the individual's cardiovascular system to produce a synchronized ECG-BCG signal set showing the effects of stress on the signal outputs. The stressed signal outputs can then be compared using at least one algorithm, to the resting-stage signal outputs for detection, quantification and assessments of stress-effected variations in the signal wave patterns and h-i-j-a-a$^1$-g-H-I-J-K-L-M-N peaks.

After acquisition, processing and extraction of BCG-ECG signal pick values and. time intervals the comparison of the time-pick values is conducted. The comparison includes the following:
1. pick values and their respective normalized amplitude values; the lower or higher values are determined in comparison of the pre and post exercise assessment,
2. the time intervals related to the pick vales are compared and the differences are derived, the differences are determined on cycle-by-cycle basis; the extreme values and the averaged values are recorded and reported.

The computer software program of the present invention may be additionally configured to average synchronized outputs for an individual's resting and stressed stages, and then to overlay the averaged synchronized outputs to enable visual observation and analyses of the cardiovascular signal outputs. Since the data for each signal recording session is storable in a data storage device, it is possible to collect resting stage signal data from an individual over an extended period of time, e.g., months or years or decades, and then precisely detect and assess physiological changes that may have occurred in the individual's resting stage cardiovascular system during these time periods.

The graphical user interface (GUI) of the present invention is configured to manage the acquisition, analysis, storage and reporting of large sets of ECG-BCG waveforms. A backend data management module may be optionally provided for efficient interfacing between the GUI and the synchronized ECG-BCG data stored in a suitable database. An additional module may be provided for computer-aided selection of the individual tailored data-analysis algorithms for analysis and synchronizing of certain types of BCG signals, and optionally, computer-selected combinations of data-analysis algorithms. It is within the scope of this invention that the GUI is suitably configured as shown in FIG. 8:

(a) to provide at least on module configured receive a plurality of signals from an individual's cardiovascular system, and then (i) process, (ii) analyze, (iii) optimize, (iv) transform, (v) synchronize, and (vi) generate at least one output comprising at least one synchronized signal wave pattern, (b) with a computer software program configured to provide a computer-aided process for selection of a suitable data-analysis algorithm for processing an incoming stream of plurality of signals from an individual's cardiovascular system, and optionally, for a selection of a combination of suitable data-analysis algorithms, and (c) to provide a data flow management module for communicating, and cooperating with a data storage device, and (d) to provide an outputs management module for communicating synchronized ECG-BCG signal outputs to devices exemplified by monitors, screens, printers and plotters.

Figure 8:
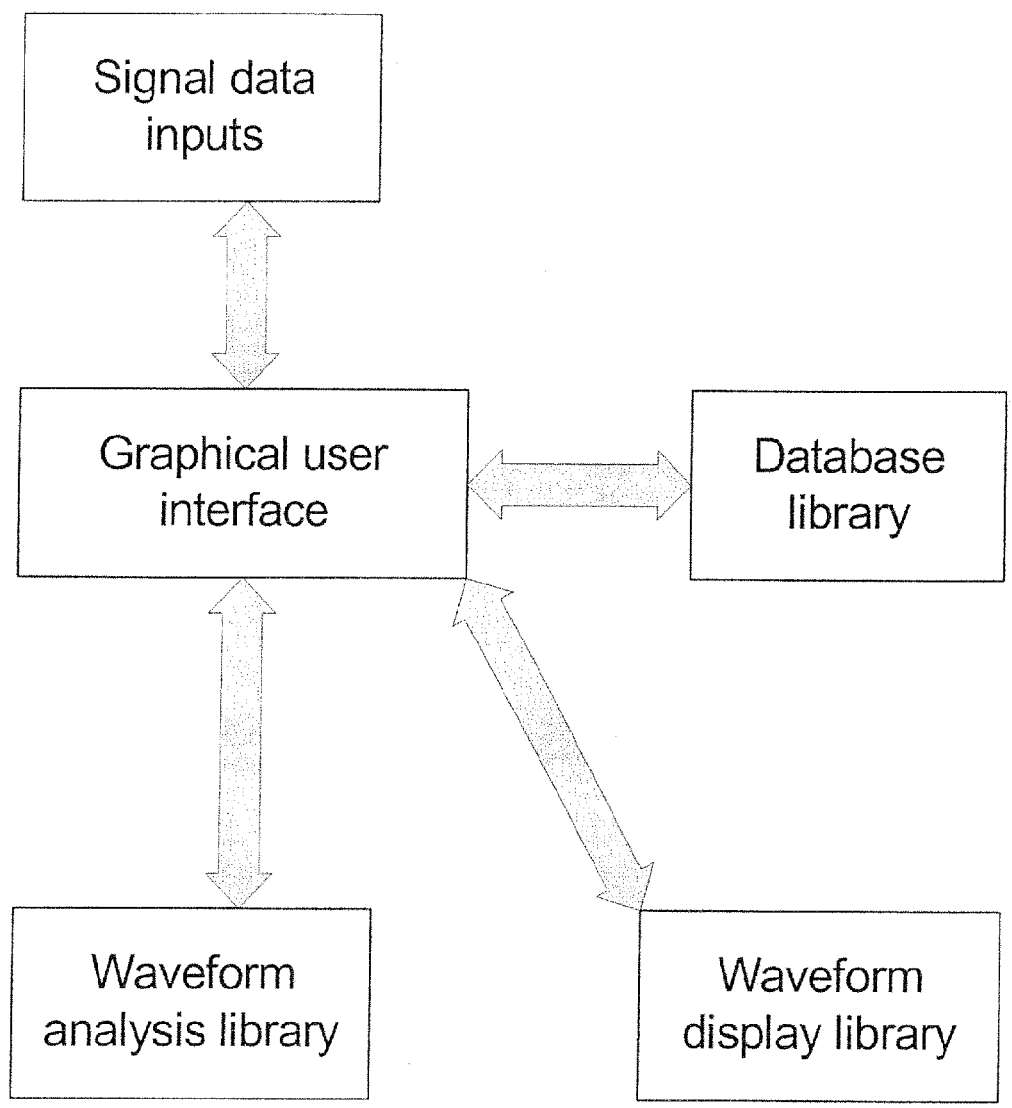
FIG. 8 is a systems flow chart showing the data flow into and out of the graphical user interface.
Figure 9:
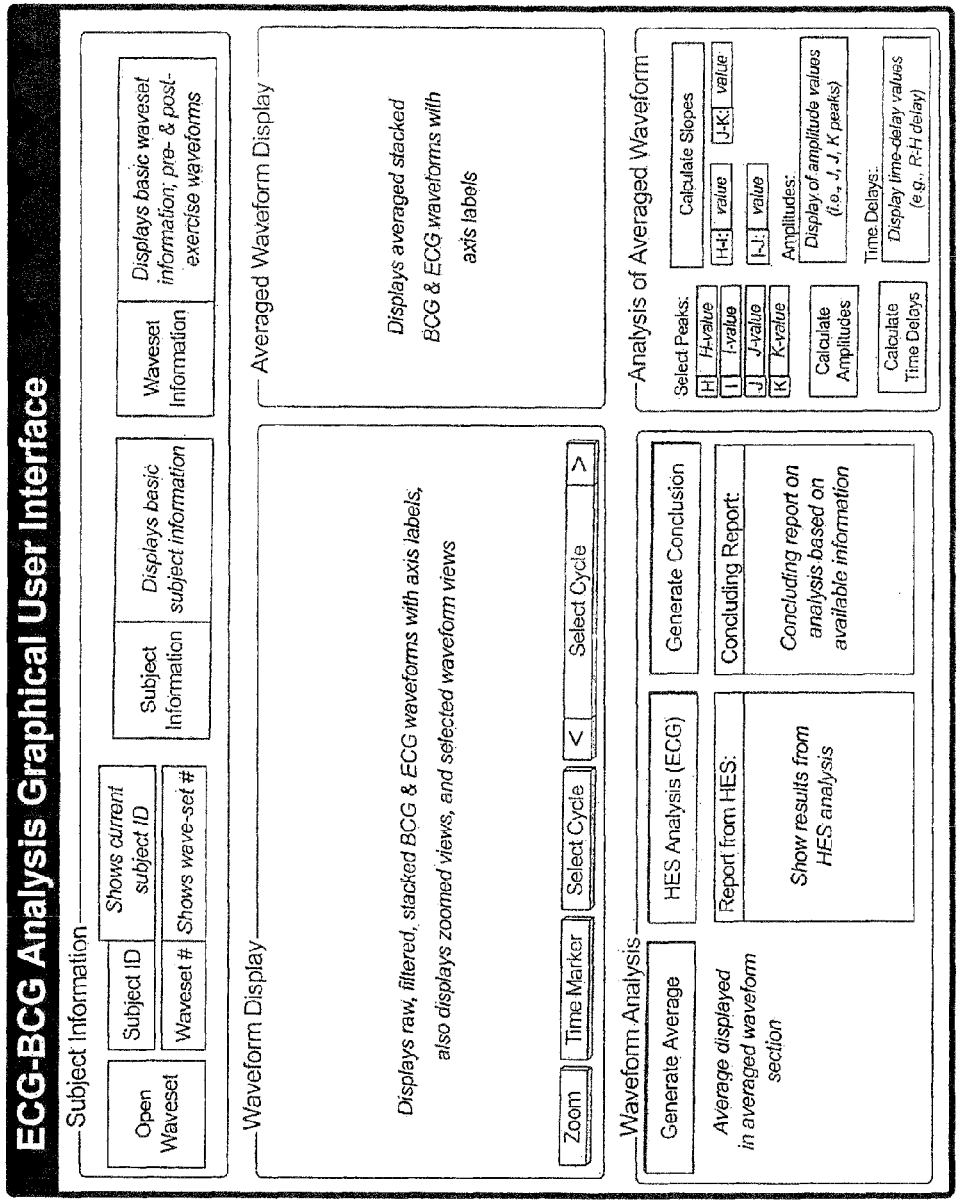
FIG. 9 is an exemplary illustration of a layout for an ECG-BCG analysis Graphical User interface (GUI) according to one aspect of the present invention.

Referring to FIG. 8, the GUI is in windows GUI format through Microsoft Foundation Class (MFC). It provides the basic system layout, waveform display, as well as various buttons, inputs, and fields associated with data management and analysis function calls FIG. 9. The GUI provides the user access to retrieve and analyze the waveforms from the database. A model GUI drawing is attached in the appendix to provide more detail to the basic design of the GUI. The database management module is a library of general functions providing the User Interface Module access to the database. Basic functions may include, "read", "write to datatable", "add subfolder", "retrieve wavefile", and "save/resave wavefile". The waveform display module suitably comprises a library of general functions. It may additionally contain basic waveform display functions such as "draw and erase waveforms", "scrolling display and zooming", "select points on waveform", "select cycles on waveform", and "get values on wavepoints". The waveform analysis module suitable comprises a library collection of functions. These functions are linkable functions that the User Interface Module can call upon to provide outputs to the waveform analysis module. The basic function groups will include algorithms to "detect wave slopes", "amplitude", "interwavelet delays", "cycle detection", "averaging", and other analysis algorithms known to those skilled in these o be useful for analyzing ECG or BCG signals.

Figure 10:
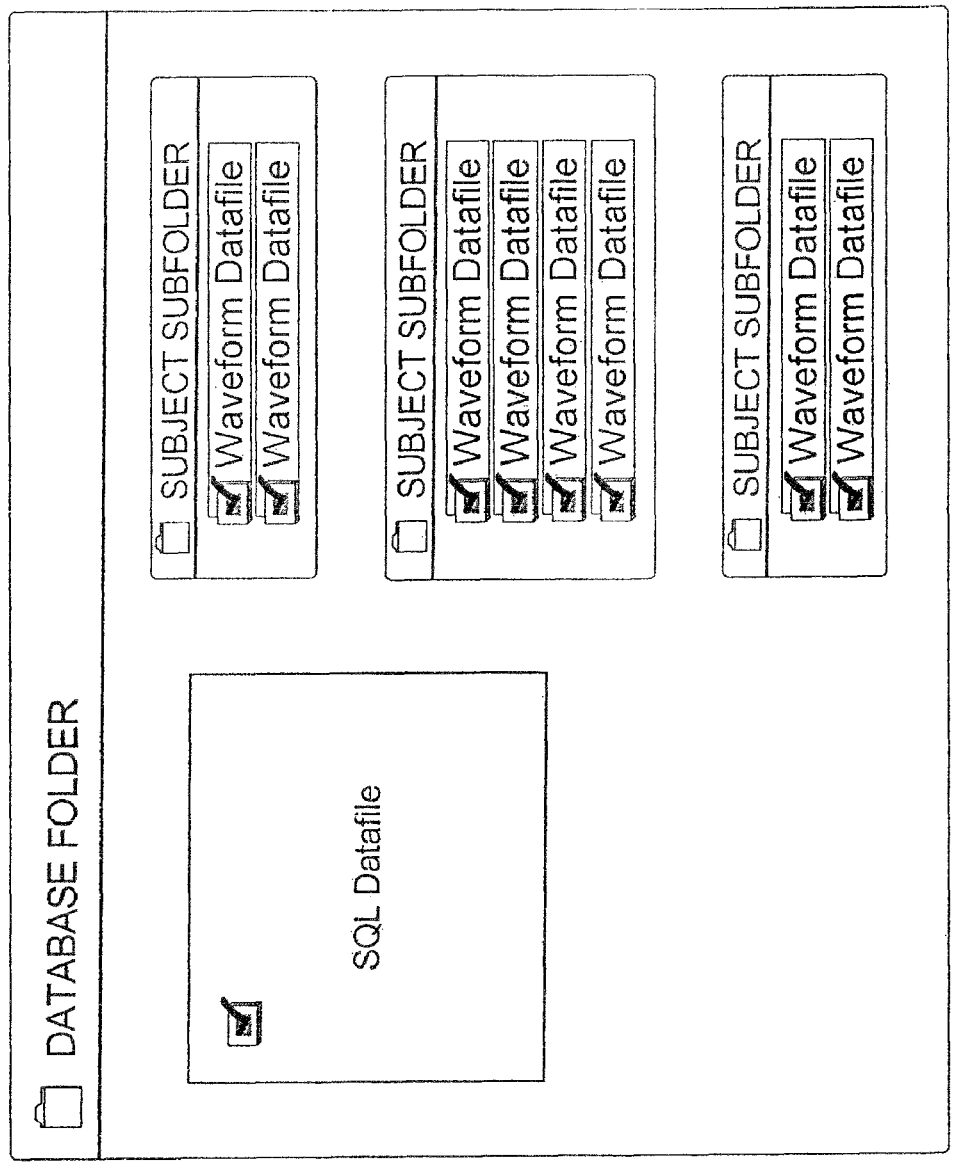
FIG. 10 is an exemplary illustration of a basic layout for a database according to one aspect of the present invention.
Figure 11:
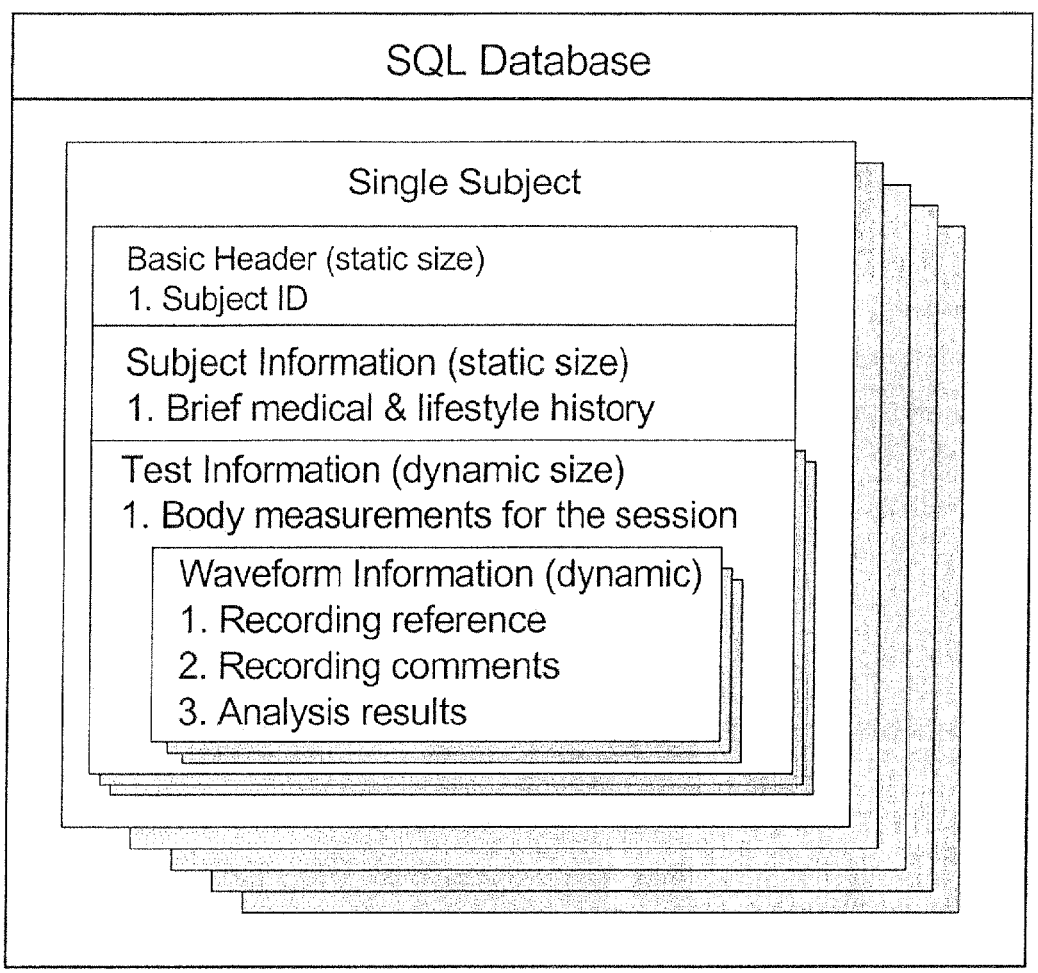
FIG. 11 is an exemplary illustration of a sample SQL data table according to one aspect of the present invention.

FIG. 10 shows an exemplary basic layout for a database structure useful to storing sets of ECG-BCG waveforms provided by the present invention. The database is contained inside a main folder, the database folder. This database folder contains a SQL (similar to Access) type data table. The SQL data table stores information for each subject and references to the waveforms associated (FIG. 11). The waveform data files for each subject are stored under subfolders located under the same main folder. There may be several waveform data files during a single session for the same subject, thus an exemplary naming convention has been established to maintain reliable referencing. The exemplary file naming convention is as follows: first, a 4-digit subject ID is placed, followed by an underscore, then the location of the BCG reading is indicated by appending either PMI (4/5-intercostal) or STR (sternal), followed by another underscore, then pre- or post-exercise reading is indicated by appending PRE (for pre-exercise) or POS (for post-exercise), followed by the number of the recording, followed by another underscore, then finally the date is appended using the year-month-date convention (YYYYMMDD). The template for the filename would read the as follows: XXXX_PMI/STR_PRE/POS#_YYYYMMDD An exemplary method for the use of the system of the present invention for monitoring the physiological condition of an individual's cardiovascular systems and for early identification cardiovascular abnormalities and malfunctions is provided below. Referring again to FIG. 5, the first step is to collect and input into the GUI, the individual's: (a) medical history relating to their cardiovascular system, (b) lifestyle characteristics such smoking, drinking, nutrition, drug use habits and other lifestyle habits, (c) physical activity level; and (d) physical and genetic information including race, weight, height, circumference of their body around the hips, circumference of their body around the waist, age, and sex. The second step is to measure their blood pressure with a suitable blood pressure measuring device exemplified by CAS Vital Signs Monitors Models 740, 750C and 750 E (CAS Medical Systems Inc., Branford, Conn., USA). It is suitable for the individual to remain interconnected with the blood pressure measuring device for the duration of the testing period. The third step is to attach an appropriate number of electrocardiograph (ECG) electrodes to appropriate sites on the individual's body and then connect the ECG electrodes to a suitable ECG system. The fourth step is for the individual to lie in a prone position after which, a suitable ballistocardiograph (BCG) accelerometer as exemplified by those supplied by Brüel Kjær (Skodsborgvej 307, DK-2850, Nærum, Denmark) is attached to the base of the individual's sternum with hypoallergenic double-sided adhesive tape. is also suitable to clip a pulseoximeter to the individual's finger. Exemplary suitable pulseoximeters include Nonin 8600 pulseoximeters (Nonin Medical. Inc., Plymouth, Minn., USA) and CAS Vital Signs Monitors Models 740, 750C and 750 E (CAS Medical Systems Inc.). The sixth step is to record the individual's resting-stage ECG, BCG, blood pressure, heart rate and blood oxygen concentration signal data for a selected period of time while they are lying in a prone position and breathing normally. An exemplary suitable resting-stage data collection period is about three minutes, but this data collection period may be adjusted as determined to be appropriate by the medical personnel conducting the testing of the individual. It is preferable that a plurality of BCG data collections is conducted during the resting-stage data collection period. A suitable number of BCG data collections during this period is three. The seventh step is for the individual to perform a selected physical exercise for a selected suitable period of time appropriate for the selected physical exercise. Exemplary suitable physical exercises include pedaling on a stationary bicycle, running or walking on a treadmill, manipulating a StairMaster® exercise device (StairMaster is a registered trademark of StairMaster Sports/Medical Products, Inc., Vancouver Wash., USA), jogging, swimming and the like. The eighth step is for the individual to lie down into a prone position immediately after the period of physical exercise has ended for recording of the individual's post-exercise ECG, BCG, blood pressure, heart rate and blood oxygen concentration signal data for a selected period of time. An exemplary suitable post-exercise data collection period is about three minutes, but this data collection period may be adjusted as determined to be appropriate by the medical personnel conducting the testing of the individual. It is preferable that a plurality of BCG data collections is conducted during the resting-stage data collection period. A suitable number of BCG data collections during this period is three.

The subject information, resting-stage, and post-exercise data inputs are transmitted to the database engine where they are stored in separate files in the database, and are accessible for processing, synchronization, and analyses by the algorithms of the present invention disclosed herein for synchronization of the R peak of the ECG signal and the H peak of the BCG signal for each set of ECG and. BCG signals concurrently collected from the individual during their rest-stage and post-exercise periods. The processed data is stored in separate files in the database, and are displayable on suitable monitors and screens, and printable by suitable printers and plotters. Comparisons of the individual's resting-stage and post-exercise synchronized ECG-BCG wave patterns generated by the algorithms of the present inventions will enable detection and assessments in stress-induced changes in the individual's BCG wave patterns and related h-i-j-a-$a^1$-g-H-I-J-K-L-M-N peaks.

In accordance with one exemplary embodiment, the system may be used as a routine testing method in a clinical environment as exemplified by a Medical Doctor's office, a walk-in clinic, a clinical laboratory, a testing facility associated with a medical research institute, a testing facility associated with a hospital, and the like.

In accordance with another exemplary embodiment, the system may be optionally adapted for employment in exercise and training facilities for observing, recording and storing changes in an individual's cardiovascular system during periods of exercise and training for the purposes of monitoring improvements in cardiovascular fitness and for detection of onset of potential cardiovascular malfunctions.

In accordance with another exemplary embodiment, resting-stage cardiovascular data and related synchronized ECG-BCG wave patterns may be collected from a plurality of individuals, compiled and stored in a database file for use as a "population" sized reference point for comparing individuals' resting-stage synchronized ECG-BCG wave patterns. It is within the scope of the present invention to separate and group pluralities of resting-stage synchronized ECG-BCG wave patterns in accordance to, for example, the Starr classification system to provide "population" sized reference groups of healthy individuals with ideal synchronized ECG-BCG wave patterns (i.e., resting-stage Class 1), individuals with somewhat less than ideal synchronized ECG-BCG wave patterns (i.e., resting-stage Class 2), individuals whose synchronized ECG-BCG wave patterns show debilitation of cardiovascular function under resting conditions (i.e., resting-stage Class 3), and individuals whose synchronized ECG-BCG wave patterns show significant debilitation of cardiovascular function under resting conditions (i.e., resting-stage Class 4).

The system and methods of the present invention for monitoring cardiovascular physiological conditions and for detecting related abnormalities and malfunctions are described in more detail in the following examples.

EXAMPLE 1

An exemplary system of the present invention was configured as shown in Fig. comprising the following components:
1. CSA 750C Multi-Parameter Monitor (CAS Medical Systems Inc.) for monitoring blood pressure, heart rate and blood oxygen levels.
2. Burdick® EK10 12 lead, single channel electrocardiograph (Cardiac Science Corp., Bothell, Wash., USA) for detection and transmission of ECG signals.
3. Brüel & Kjær® (Brüel & Kjær is a registered trademark of Brüel & Kjær Sound & Vibration; Measurement A/S, Nærum, Denmark) Type 4381 accelerometer coupled with a Brüel & Kjær® Type 2635 charge amplifier for detection and transmission of BCG signals.
4. LabVIEW® (Lab VIEW is a registered trademark of National Instruments Corp., Austin, Tex., USA) 8.2 data acquisition system installed on an IBM laptop computer, for concurrently receiving ECG and BCG signals from the ECG and BCG instruments
5. A software program comprising the algorithms described herein for conditioning and synchronizing ECG and BCG, and configured to communicate with the LabVIEW® 8.2 data acquisition system.
6. A database program configured to receive, store and display conditioned raw and synchronized ECG and BCG signal sets.
7. A stationary exercise cycle.

The system was used to collect, condition, synchronize, process, analyze, store and report resting-stage and post-exercise cardiovascular data from 142 individuals. Each individual was assessed for a period of 30 minutes as follows: First, their medical history was filled in on a questionnaire comprising the following questions:
(1) medical history of their heart (including all know heart conditions),
(2) lifestyle habits (i.e. smoking drinking, drug use, stress levels, etc.),
(3) physical activity level,
(4) race,
(5) weight,
(6) height,
(7) hip circumference,
(8) waist circumference,
(9) body fat %,
(10) age, and
(11) sex.

Next, the individual's blood pressure was recorded after which, ECG electrodes to both of their shoulders and just above both hips, after which the electrodes were attached to the Burdick® EK10 electrocardiograph. Then, the Brüel & Kjær® Type 4381 accelerometer and Type 2635 charge amplifier were attached with hypoallergenic double-sided adhesive tape to the base of the individual's sternum. Then, the pulseoximeter provided with the CSA 750C Multi-Parameter Monitor was clipped onto one of the individual's forefingers and connected to the Monitor. The individual then lay very still in a prone position on a padded board while breathing normally while three 1-minute-long BCG recordings were collected, with 1-minute rest periods between each 1-minute recording period. The pulseoximeter, ballistocardiography, ECG. and blood pressure equipment were disconnected from the individual who was then asked to pedal the stationary exercise cycle for a 1-minute period or alternatively, depending on the physical condition of the individual, walk around a set course for 1 minute. They were then asked to again to lie down very still in a prone position on the padded board while the equipment was reconnected to the individual for collection of post-exercise blood pressure, heart rate, blood oxygen concentration, ECG signals plus three 1-minute BCG recordings, with 1-minute rests periods between each 1-minute recording period.

The resting-stage and post-exercise ECG and BCG signals were conditioned by (a) passing the ECG signals through a fifth-order Butterworth filter with the high-pass cutoff frequency set at about 40 HZ and the low-pass filter set at about 1 Hz, and (b) passing the BCG signals through a fifth-order Butterworth filter with the high-pass cutoff frequency set at about 25 Hz and the low-pass frequency set at about 1 Hz. The algorithms described herein were applied to each ECG-BCG signal sets to (a) identify the R peaks, (b) synchronize the H peaks with the R peaks, (b) parsing the conditioned BCG signals to locate and mark the h-i-j-a-a1-g and I-J-K-L-M-N peaks, and then, (c) averaging the conditioned resting-stage and post-exercise BCG signals.

EXAMPLE 2

Figures 12A, 12B:
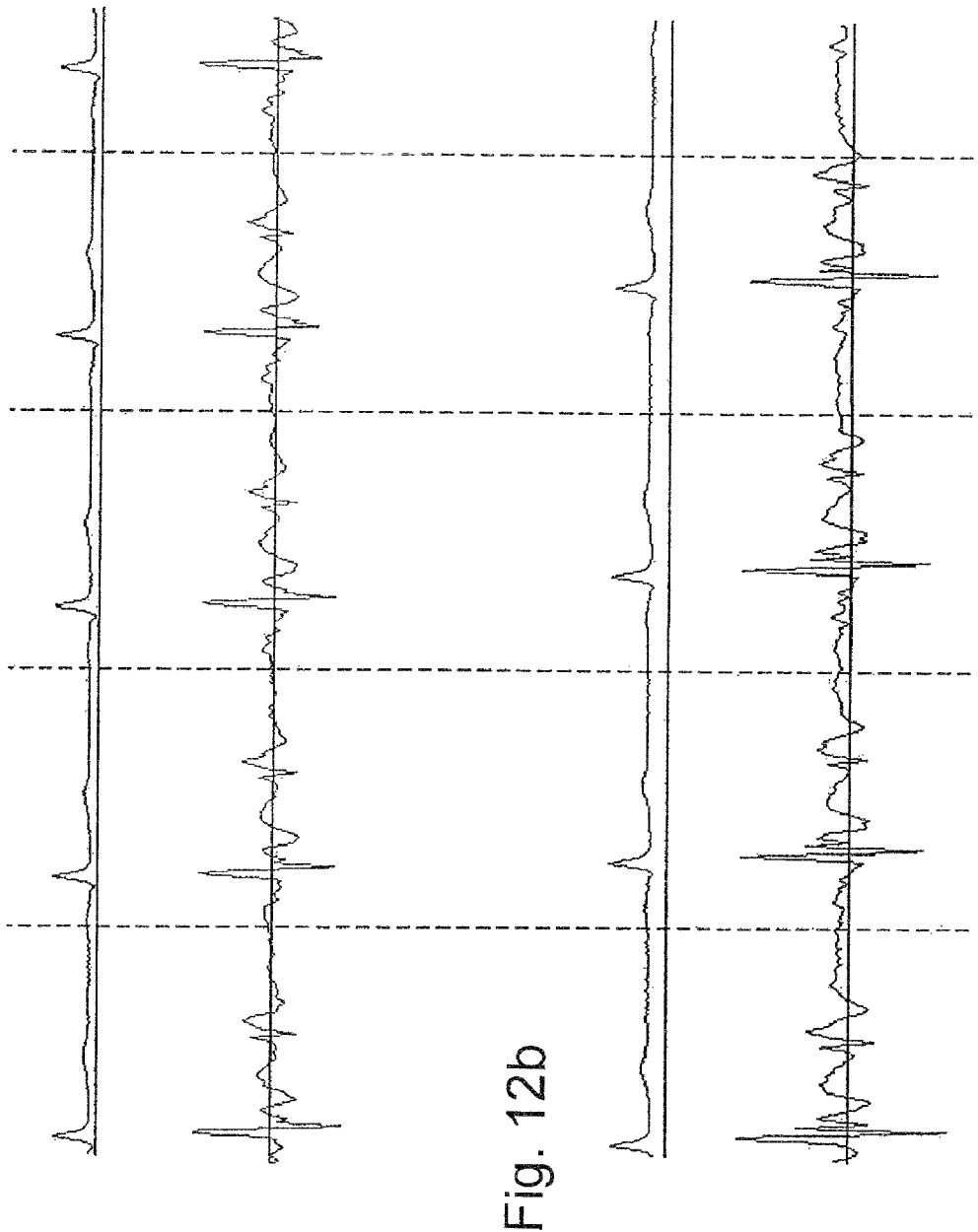
Figure 13A:
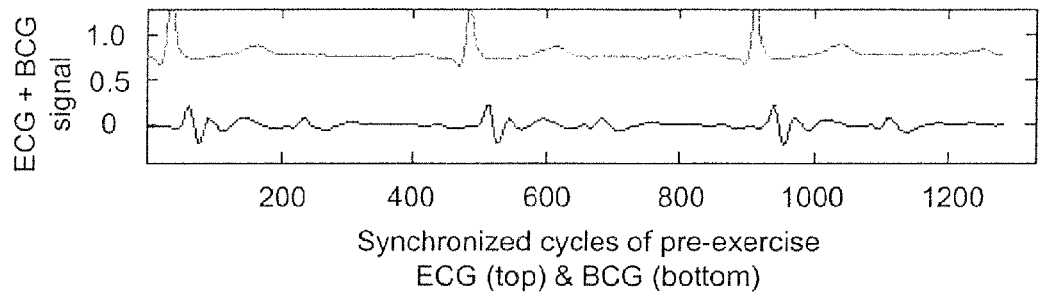
FIG. 13a shows the resting stage ECG-BCG signal set from FIG. 12a after conditioning and synchronization according to one aspect of the present invention.
Figure 13B:
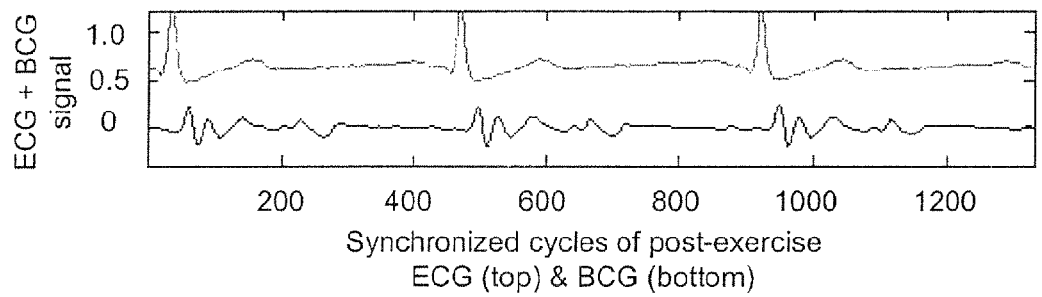
FIG. 13b shows the post-exercise ECG-BCG signal set from FIG. 12b after conditioning, and synchronization.
Figure 13C:
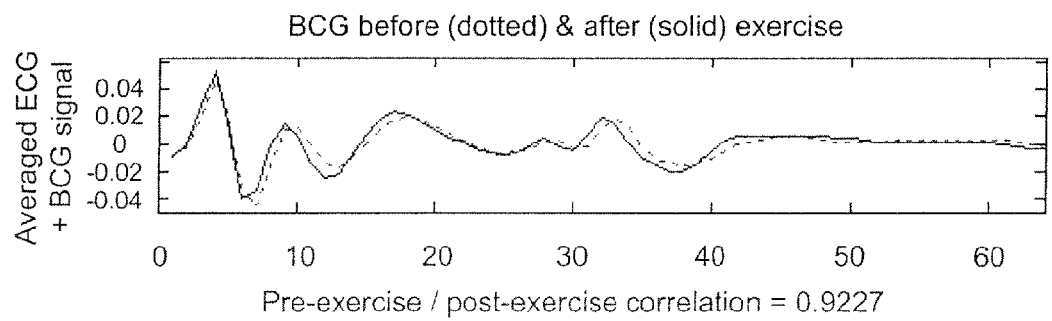
FIG. 13c shows the synchronized post-exercise BCG signal overlaid onto the synchronized pre-exercise resting-stage BCG signal.

FIG. 12a shows the raw; unconditioned ECG and BCG signals produced by a healthy individual with a normally function cardiovascular system, during a pre-exercise non-stressed resting-stage period. Additional cardiophysiological data collected as described in Example 1, were stored in the system's database. FIG. 12b shows the raw, unconditioned ECG and BCG signals produced by the same individual after a period of physical exercise administered as outlined in Example 1. The R-peaks of the ECG signal during the pre-exercise resting stage (FIG. 12a) were used by the heuristic algorithms to mark and synchronize the BCG H-peaks with said concurrently collected ECG R-peaks. The heuristic algorithms subsequently marked and correlated the subsequent I-J-K-L-M-N peaks and produced the synchronized ECG-BCG cycle patterns shown in FIG. 13a. In a similar way, the R-peaks of the ECG signal during the post-exercise stage (FIG. 12b) were used by the heuristic algorithms to mark and synchronize algorithms subsequently marked and correlated the subsequent I-J-K-L-M-N peaks and produced the synchronized ECG-BCG cycle patterns shown in FIG. 13b. Finally, the software program compared and assessed synchronized BCG patterns to determined if significant changes occurred in the physical functioning of the various heart components as exemplified by the vigor of cardiac ejection of blood from the atria and ventricles, and the speed of filling of the atrial chambers during the diastolic period, and the related physical movements of the heart muscles, valves, and related flows of blood into, between and out of the atria and ventricles. FIG. 13c shows a comparison of the pre-exercise and post-exercise synchronized BCG signals produced by the exemplary system of the present during one cycle, i.e. heart beat. In this healthy individual, the pre- and post-exercise BCG patterns are identical showing that the electrical, physical and physiological components of the heart were not affected by the application of stress.

EXAMPLE 3

Figure 14A:
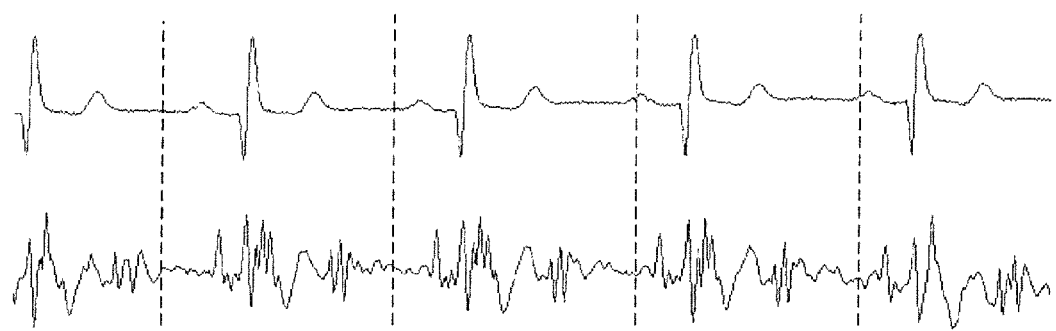
Figure 14B:
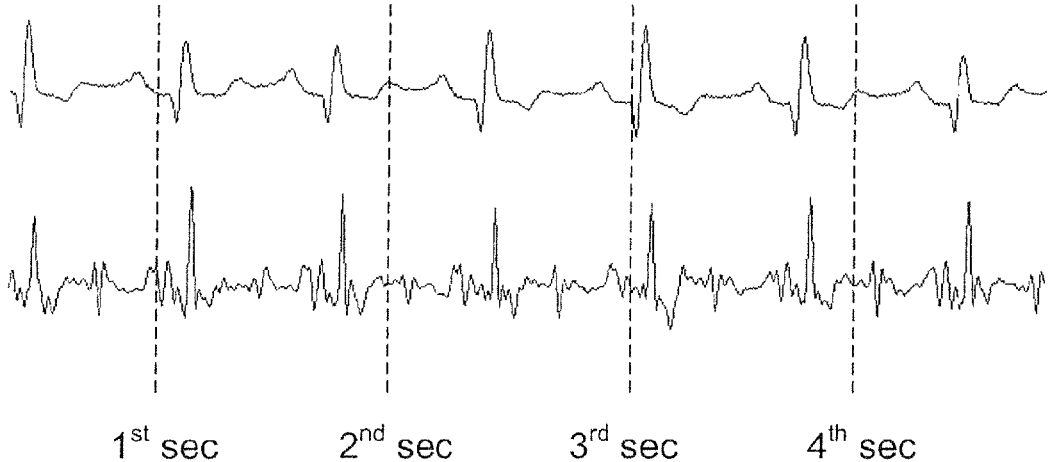
FIG. 14b shows a raw unconditioned and unsynchronized ECG-BCG signal set collected from the unhealthy individual during the post-exercise period.
Figure 15A:
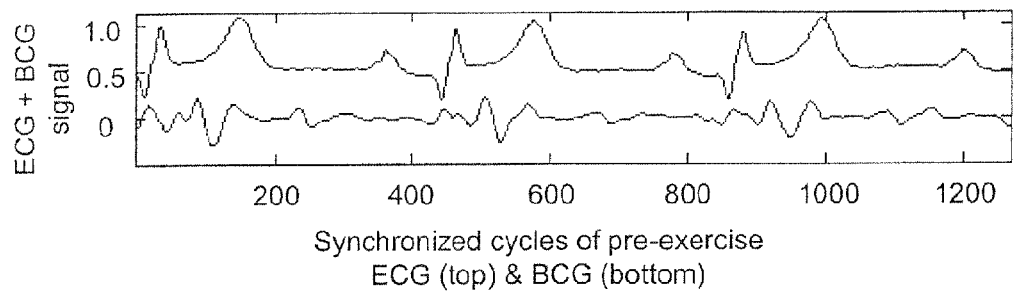
FIG. 15a shows the resting stage ECG-BCG signal set from FIG. 14a after conditioning and synchronization according to one aspect of the present invention.
Figure 15B:
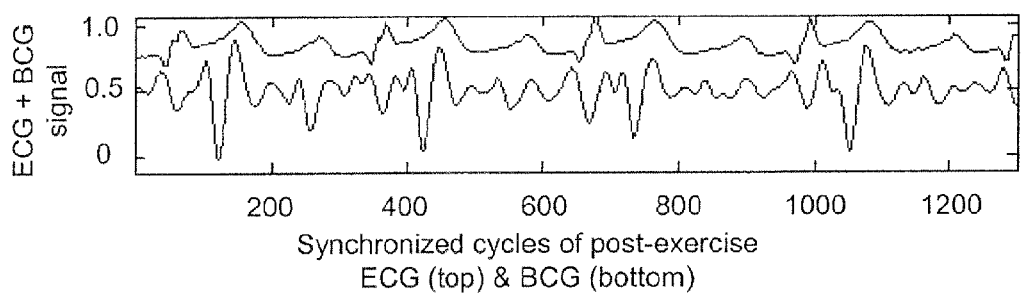
FIG. 15b shows the post-exercise ECG-BCG signal set from FIG. 14b after conditioning and synchronization.

FIGS. 14a and 14b show the raw, unconditioned ECG and BCG signals produced by an individual before and after stress induced by physical exercise as described in Example 1. This individual had previously experience and recovered from a mild heart attack, and is in the process of modifying their lifestyle in order to strengthen their cardiovascular system. This individual's post-exercise heart rate was about 65%-70% (5 beats in a 3-second interval) greater than the pre-exercise rate (3 beats in a 3-second interval) (FIGS. 14a and 14b). More significant, however, are the changes that are evident after the signal conditioning to remove the background noise and synchronization of the BCG signals with the ECG signals (FIGS. 15a and 15b), that show the increased heart rates is accompanied by increased physical intensities in the movements of the heart muscles and valves (FIG. 15b). However, comparison of the pre- and post-exercise synchronized BCG signals show that the H-I-J-K-L-K-M-N peaks in the pre-exercise BCG signal pattern, the peaks between the H-I-J-K-L-K-M-N are flattened out and that the demarcation between the peaks is significantly diminished (FIG. 15a). However, their post-exercise synchronized. BCG signal (FIG. 15b) shows that a clearly distinguishable H-I-J-K pattern was temporarily reestablished, presumably for a brief period of time to supply an increased supply of oxygen to the heart muscles. However, the presence of this "normal-appearing" BCG pattern during the post-exercise period suggests that this individual has the potential to restore his cardiovascular system to approximate the functioning of the individual tested in Example 2. So, although in this example, the individual's raw unconditioned pre- and post-exercise ECG and BCG signals appeared to be normal although with an elevated heart rate, the system and the software of the present invention provided the means for detecting physiological abnormalities associated with physical malfunctioning with one or more of their heart valves, heart muscles and vascular system. Furthermore, it is within the scope of this invention to store such data produced by an individual during sampling periods over extended periods of time, so that improvements in the individual's cardiovascular system's function and capacity can be recorded and reported as part of treatment, therapy, exercise programs and the like.

EXAMPLE 4

Figure 16A:
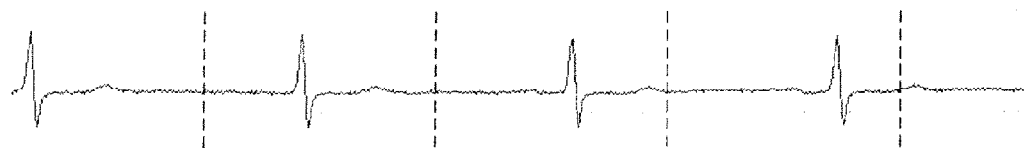
Figure 16B:
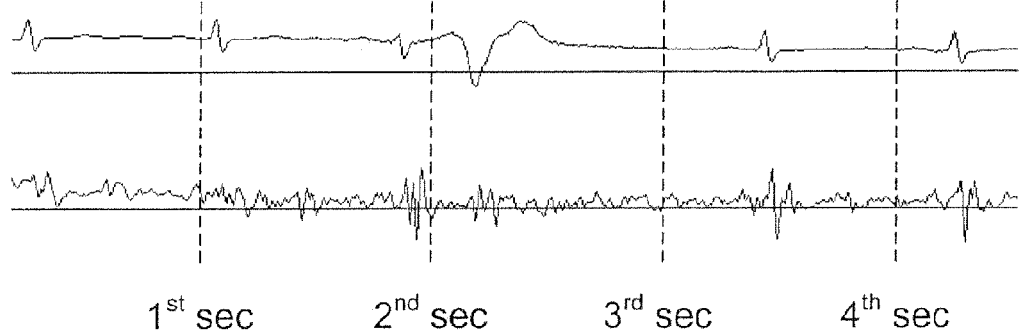
FIG. 16b shows a raw unconditioned and unsynchronized ECG-BCG signal set collected from the at-risk individual during the post-exercise period.
Figure 17A:
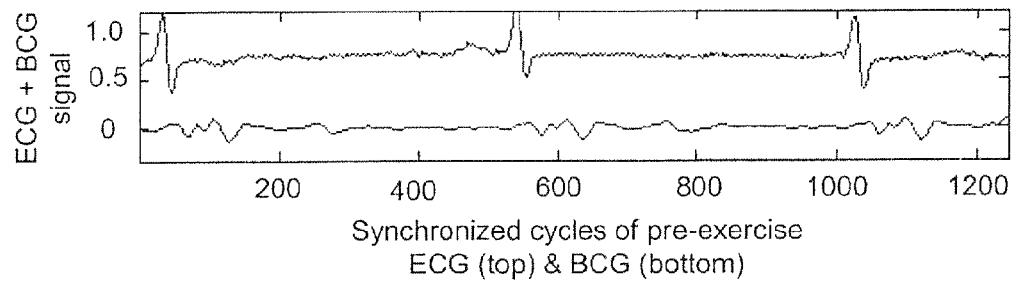
FIG. 17a shows the resting stage ECG-BCG signal set from FIG. 16a after conditioning and synchronization according to one aspect of the present invention.
Figure 17B:
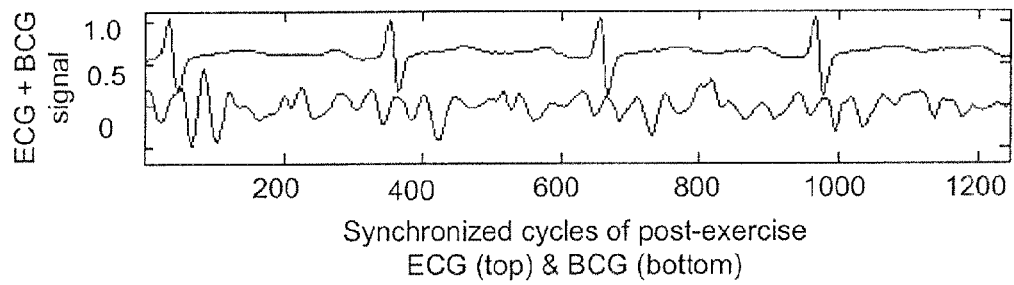
FIG. 17b shows the post-exercise ECG-BCG signal set from FIG. 16b after conditioning and synchronization.
Figure 17C:
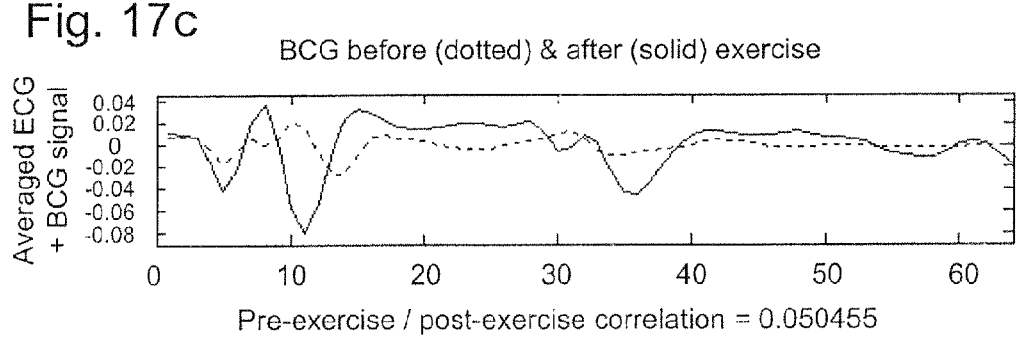
FIG. 17c shows the synchronized post-exercise BCG signal overlaid onto the synchronized pre-exercise resting-stage BCG signal.

FIGS. 16a and 16b show the raw, unconditioned ECG and BCG signals produced by an individual before and after stress induced by physical exercise as described in Example 1. This individual is considered at-risk based on the sporadic breakdown in their post-exercise ECG signal (FIG. 16b) in conjunction with the substantial decreases in the amplitudes of the BCG signals (FIG. 16b). However, conditioning the ECG and BCG signals and synchronizing the BCG signal with the ECG signal showed that, during the pre-exercise resting period, the magnitude of the BCG H-I-J-K-L-K-M-N peaks are even more diminished than was seen with the unhealthy individual in Example 3 with only the H-I wave clearly identifiable (FIGS. 17a and 17c). Although the intensity of the BCG peaks increased post-stress (FIG. 17b), the amplitudes of the peaks within the wave pattern were approximately the same suggesting that even under stress, the post-right-ventricular contraction movements of the heart produce as much signal amplitude as do the septum recoil (i.e., the H-I wave) and flow of blood into the pulmonary and aortic arteries (i.e., J-K wave). In a healthy individual as exemplified in Example 2 (FIG. 13b), the amplitudes of the H-I and J-K waves are typically greater than subsequent L-M-N waves.

EXAMPLE 5

Figure 15C:
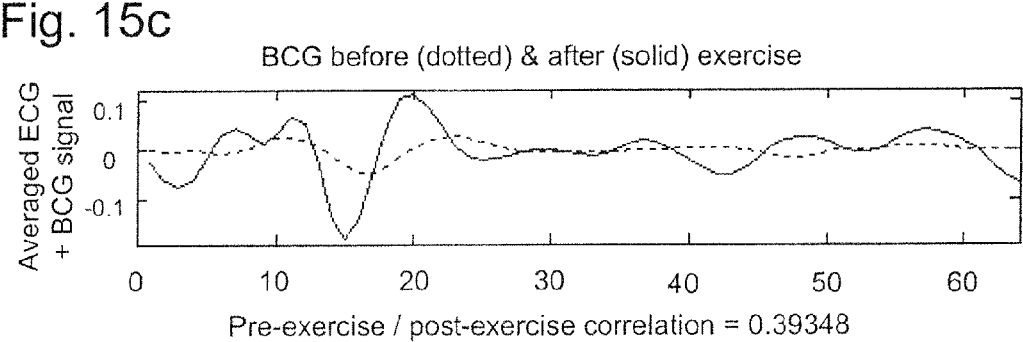
FIG. 15c shows the synchronized post-exercise BCG signal overlaid onto the synchronized pre-exercise resting-stage BCG signal.

FIGS. 18a, 18b, and 18c compare the conditioned synchronized pre- and post exercise BCG signals from a healthy individual (FIG. 18a is taken from FIG. 13c), an unhealthy individual (FIG. 18b is taken from FIG. 15c) and an at-risk individual (FIG. 18c is taken from FIG. 17c). As previously discussed, the healthy individual's pre- and post-exercise synchronized BCG wave patterns are identical (FIG. 18a). The unhealthy individual's pre-exercise BCG wave pattern (FIG. 18b) has substantially diminished H, J, and L peaks accompanied by flattened and elongated H-I and J-K waves (exemplified by $H^1$, $I^1$, $J^1$ and $K^1$) while after exercise, the amplitudes of the H, J, and L peaks increase considerably, the H-I and J-K waves are more clearly defined, and the L-M-N waves appear (exemplified by $H^2$, $I^2$, $J^2$, $K^2$, $L^2$, $M^2$, $N^2$). The at-risk individual's pre-exercise BCG wave pattern exemplified by $H^1$, $I^1$, $J^1$ and $K^1$ peaks (FIG. 18c) is similar to the unhealthy individual's pre-exercise BCG wave (FIG. 18b). However, the at-risk individual's post-exercise BCG wave pattern exemplified by $H^2$, $I^2$, $J^2$, $K^2$, $L^2$, $M^2$, $N^2$ peaks (FIG. 18c) is different from the unhealthy individual's BCG wave pattern (FIG. 18b) indicating that different components of the at-risk individual's cardiovascular system are abnormal relative to the unhealthy individual's system, both systems in comparison to the healthy individual's system as exemplified by the post-exercise BCG wave pattern in FIG. 18a. Those skilled in these arts will understand that storing such data in a database for future reference to in comparison with later collected ECG and BCG data with the exemplary systems of the present invention, will enable: (1) assessments of the improvements or deterioration in an individual's cardiovascular system over a period of time, and also, (2) comparisons of the responses of an individual's cardiovascular systems pre- and post-stress to abroad population database.

While this invention has been described with respect to the exemplary embodiments, those skilled in these arts will understand how to modify and adapt the systems, methods, algorithms and heuristic methods disclosed herein for monitoring the physiological condition of cardiovascular systems and for detecting abnormalities and malfunctions therein by conditioning and synchronizing exemplary ECG and BCG signals for other applications. For example, the system of the present invention may be additionally provided with an implantable device configured for installation within an individual's body and for receiving therein electrical signals derived from the conditioned and synchronized ECG-BCG signal sets, and for transmitting the derived electrical signals to a target site within the individual's body for affecting a physiological response therein. Furthermore, it is possible for those skilled in these arts to adapt the systems, methods and algorithms disclosed herein for monitoring: the physiological condition of other types of mammalian systems wherein a plurality of detectable signals are generated whereby the signals are acquired, processed, synchronized and retransmitted for storage and/or reporting and/or for providing returning stimulatory signals to the originating mammalian systems. Examples of such modifications include providing alternative types of paired signals for condition and synchronization as exemplified by signals quantifying levels of blood sugar paired with signals for example quantifying blood oxygen levels or alternatively, insulin levels, or alternatively, electrical impulses transmitted by the peripheral nervous system paired with electrical impulses transmitted by the central nervous systems, or further alternatively, with signals generated by systemic antibodies to various and individual types of cancers paired with signals generated by selected systemic biochemical markers such as proteins, and the like. Therefore, it is to be understood that various alterations and modifications can be made to the systems, methods and algorithms disclosed herein for monitoring the physiological condition and detecting abnormalities therein, within the scope of this invention.

We claim:

1. A method for determining one or more parameters characteristic of an individual's cardiac function, said method comprising:
   acquiring electrocardiograph and ballistocardiograph signals from said individual;
   converting said electrocardiograph and ballistocardiograph signals into electrocardiograph data and ballistocardiograph data;
   receiving said electrocardiograph data and ballistocardiograph data at a computer, said computer including a microprocessor;
   synchronizing, by said microprocessor, said electrocardiograph data with said ballistocardiograph data to provide at least one synchronized electrocardiograph-ballistocardiograph waveform;
   identifying, by said microprocessor, one or more components of said synchronized electrocardiograph-ballistocardiograph waveform, said components indicative of said one or more parameters characteristic of an individual's cardiac function.

2. The method according to claim 1, wherein identifying one or more components of the synchronized electrocardiograph-ballistocardiograph waveform comprises detecting and marking one or more of the h, i, j, a, $a^1$, g, H, I, J, K, L, M and N peaks on said synchronized electrocardiograph-ballistocardiograph waveform.

3. The method according to claim 1, wherein said one or more parameters are one or more of: time period between any two of the h, i, j, a, $a^1$, g, H, I, J, K, L, M and N peaks, time duration of the H-I wave, H-I slope, I-J slope, J-K slope, K-L slope, L-M slope, M-N slope, amplitude of the H peak, amplitude of the I peak, amplitude of the J peak, amplitude of the K peak, amplitude of the L peak, amplitude of the M peak, amplitude of the N peak, amplitude of the j peak, amplitude of the $a^1$ peak and j-a slope.

4. The method according to claim 1, wherein said one or more parameters are one or more of: stroke volume, cardiac output, ending diastolic volume, ending systolic volume, ventricular ejection fraction, cardiac output index, pre-ejection period, cardiac performance index and isovolumetric contraction time.

5. The method according to claim 1, wherein converting said electrocardiograph and ballistocardiograph signals into electrocardiograph data and ballistocardiograph data comprises converting, by an analog-digital converter, analog electrocardiograph and ballistocardiograph signals into digital electrocardiograph and ballistocardiograph data.

6. The method according to claim 1, wherein said ballistocardiograph signals are acquired from an accelerometer.

7. The method according to claim 6, wherein said accelerometer is positioned on the sternum of said individual.

8. The method according to claim 1, wherein synchronizing said electrocardiograph data with said ballistocardiograph data includes aligning an R peak of at least one electrocardiograph waveform corresponding to said electrocardiograph data with an H peak of at least one ballistocardiograph waveform corresponding to said ballistocardiograph data.

9. The method according to claim 1, further comprising comparing one or more components of said synchronized electrocardiograph-ballistocardiograph waveform with reference data.

10. The method according to claim 1, further comprising conditioning said electrocardiograph signals.

11. The method according to claim 10, wherein said conditioning comprises passing said electrocardiograph signals through a filter having a high-pass cutoff frequency of about 40 Hz.

12. The method according to claim 10, wherein said conditioning comprises passing said electrocardiograph signals through a low-pass filter of about 1 Hz.

13. The method according to claim 1, further comprising conditioning said ballistocardiograph signals.

14. The method according to claim 13, wherein said conditioning comprises passing said ballistocardiograph signals through a filter having a high-pass cutoff frequency of about 25 Hz.

15. The method according to claim 13, wherein said conditioning comprises passing said ballistocardiograph signals through a low-pass filter of about 1 Hz.

16. The method according to claim 1, further comprising generating an output providing a visual representation of said one or more parameters characteristic of said individual's cardiac function.

17. A system for determining one or more parameters characteristic of an individual's cardiac function, said system comprising:
   a first device for detecting and transmitting electrocardiograph signals of said individual, said first device comprising an electrocardiograph;
   a second device for detecting and transmitting ballistocardiograph signals of said individual, said second device comprising an accelerometer;
   an analog-digital converter in communication with said first device and said second device for converting said electrocardiograph signal into electrocardiograph data and for converting said ballistocardiograph signal into ballistocardiograph data;
   a microprocessor in communication with said analog-digital converter, said microprocessor configured to receive said electrocardiograph data and said ballistocardiograph data, synchronize said electrocardiograph data with said ballistocardiograph data to provide at least one synchronized electrocardiograph-ballistocardiograph waveform, and identify one or more components of said synchronized electrocardiograph-ballistocardiograph waveform, said components indicative of said one or more parameters characteristic of an individual's cardiac function.

18. The system according to claim 17, wherein said one or more parameters are one or more of: time period between the I peak and the L peak, time duration of the H-I wave, H-I slope, I-J slope, J-K slope, K-L slope, L-M slope, M-N slope, amplitude of the H peak, amplitude of the I peak, amplitude of the J peak, amplitude of the K peak, amplitude of the L peak, amplitude of the M peak, amplitude of the N peak, amplitude of the j peak, amplitude of the $a^1$ peak and j-a slope.

19. The system according to claim 17, wherein said one or more parameters are one or more of: stroke volume, cardiac output, ending diastolic volume, ending systolic volume, ventricular ejection fraction, cardiac output index, pre-ejection period, cardiac performance index and isovolumetric contraction time.

20. The system according to claim 17, wherein the accelerometer is configured to be positioned on the sternum of said individual.

21. The system according to claim 17, wherein synchronizing said electrocardiograph data with said ballistocardiograph data includes aligning an R peak of at least one electrocardiograph waveform corresponding to said electrocardiograph data with an H peak of at least one ballistocardiograph waveform corresponding to said ballistocardiograph data.

22. The system according to claim 17, further comprising a database in communication with said microprocessor, said database for storing said electrocardiograph data and said ballistocardiograph data.

23. The system according to claim 17, wherein said microprocessor is further configured to generate an output providing a visual representation of said one or more parameters characteristic of said individual's cardiac function.

24. The system according to claim 23, further comprising a device for displaying said output, said device selected from the group consisting of: monitors, screens, printers and plotters.

25. The system according to claim 17, further comprising a graphical user interface in communication with said microprocessor, said graphical user interface for allowing operator input.

26. The system according to claim 17, further comprising one or more filters for conditioning said electrocardiograph signals and/or said ballistocardiograph signals.

27. The system according to claim 26, wherein said filters comprise a filter having a high-pass cutoff frequency of about 40 Hz for conditioning said electrocardiograph signals.

28. The system according to claim 26, wherein said filters comprise a low pass filter of about 1 Hz for conditioning said electrocardiograph signals.

29. The system according to claim 26, wherein said filters comprise a filter having a high-pass cutoff frequency of about 25 Hz for conditioning said ballistocardiograph signals.

30. The system according to claim 26, wherein said filters comprise a low pass filter of about 1 Hz for conditioning said ballistocardiograph signals.

* * * * *

UNITED STATES PATENT AND TRADEMARK OFFICE
CERTIFICATE OF CORRECTION

PATENT NO. : 8,251,911 B2
APPLICATION NO. : 12/956643
DATED : August 28, 2012
INVENTOR(S) : David MacQuarrie et al.

It is certified that error appears in the above-identified patent and that said Letters Patent is hereby corrected as shown below:

In the Specifications:

Column 2,
Line 58, "from. the" should read --from the--

Column 5,
Line 23, "rhythm electrical functions" should read --rhythmic electrical functions--

Column 9,
Line 12, "(the j-K slope)" should read --(the J-K slope)--

Column 9,
Line 33, "between the 1-peak" should read --between the I peak--

Column 10,
Line 33, "the L-peak) ET, The" should read --the L-peak) / ET. The--

Column 10,
Lines 59-60, "calculation of the slope, the slope, the J-K slope" should read --calculation of the H-I slope, the I-J slope, the J-K slope,--

Column 11,
Line 47, "the H-I, I-J, J-K, K-L, and M-N slopes" should read --the H-I, I-J, J-K, K-L, L-M, and M-N slopes--

Column 15,
Line 2, "value of BCG" should read --value of BCG signal,--

Signed and Sealed this
Twentieth Day of November, 2012

David J. Kappos
*Director of the United States Patent and Trademark Office*

CERTIFICATE OF CORRECTION (continued)
U.S. Pat. No. 8,251,911 B2

Column 15,
Line 64, "in these o be useful" should read --in these arts to be useful--

Column 17,
Line 48, "adhesive tape. is also suitable" should read --adhesive tape. It is also suitable--

Column 20,
Line 21, "h-i-j-a-a1-g" should read --h-i-j-a-a$^{1}$-g--

Column 21,
Line 17, "synchronized. BCG signal" should read --synchronized BCG signal--